(12) United States Patent
Gregory et al.

(10) Patent No.: US 9,382,266 B2
(45) Date of Patent: Jul. 5, 2016

(54) RAPAMYCIN ANALOGUE

(71) Applicant: BUCK INSTITUTE FOR RESEARCH ON AGING, Novato, CA (US)

(72) Inventors: Matthew Alan Gregory, Cambridge (GB); Steven James Moss, Cambridge (GB); Barrie Wilkinson, Cambridge (GB)

(73) Assignee: BUCK INSTITUTE FOR RESEARCH ON AGING, Novato, CA (US)

( * ) Notice: Subject to any disclaimer, the term of this patent is extended or adjusted under 35 U.S.C. 154(b) by 0 days.

(21) Appl. No.: 14/367,181

(22) PCT Filed: Dec. 21, 2012

(86) PCT No.: PCT/GB2012/053228
§ 371 (c)(1),
(2) Date: Jun. 19, 2014

(87) PCT Pub. No.: WO2013/093493
PCT Pub. Date: Jun. 27, 2013

(65) Prior Publication Data
US 2015/0210714 A1    Jul. 30, 2015

(30) Foreign Application Priority Data
Dec. 23, 2011  (GB) .................................. 1122305.4

(51) Int. Cl.
*C07D 498/16*  (2006.01)
*A61K 31/436*  (2006.01)
*C07D 498/18*  (2006.01)

(52) U.S. Cl.
CPC ............ *C07D 498/16* (2013.01); *A61K 31/436* (2013.01); *C07D 498/18* (2013.01)

(58) Field of Classification Search
USPC .......................................... 514/291; 540/456
See application file for complete search history.

(56) References Cited

U.S. PATENT DOCUMENTS

| | | | |
|---|---|---|---|
| 7,183,289 B2 | 2/2007 | Zhang et al. | |
| 7,300,942 B2 | 11/2007 | Gregory et al. | |
| 7,390,895 B2 * | 6/2008 | Gregory et al. | 540/456 |
| 7,648,996 B2 | 1/2010 | Beckmann et al. | |
| 7,655,673 B2 | 2/2010 | Zhang et al. | |
| 7,803,808 B2 * | 9/2010 | Gregory et al. | 514/291 |
| 2005/0272132 A1 | 12/2005 | Gregory et al. | |
| 2006/0205757 A1 * | 9/2006 | Zhang | A61K 31/4745 514/291 |
| 2007/0184075 A1 | 8/2007 | Zhang et al. | |
| 2008/0188511 A1 | 8/2008 | Beckmann et al. | |
| 2009/0253732 A1 | 10/2009 | Gregory et al. | |

FOREIGN PATENT DOCUMENTS

| | | |
|---|---|---|
| GB | 1122305.4 | 12/2011 |
| WO | WO 2004/007709 A2 | 1/2004 |
| WO | WO 2006/016167 A2 | 2/2006 |
| WO | WO 2006/095185 A1 | 9/2006 |
| WO | WO 2013/093493 A1 | 6/2013 |

OTHER PUBLICATIONS

PCT International Search Report and Written Opinion dated Feb. 27, 2013 issued in PCT/GB2012/053228.
PCT International Preliminary Report on Patentability dated Jul. 3, 2014 issued in PCT/GB2012/053228.
EP Communication pursuant to Rules 161(1) and 162 EPC dated Sep. 10, 2014 issued in EP 12806101.7.
Response to EP Communication pursuant to Rules 161(1) and 162 EPC dated Mar. 20, 2015 issued in EP 12806101.7.

* cited by examiner

*Primary Examiner* — Kristin Vajda
(74) *Attorney, Agent, or Firm* — Tom Hunter; Weaver Austin Villeneuve & Sampson LLP

(57) ABSTRACT

There is provided inter alia a compound of formula (I) or a pharmaceutically acceptable salt thereof and its use in therapy.

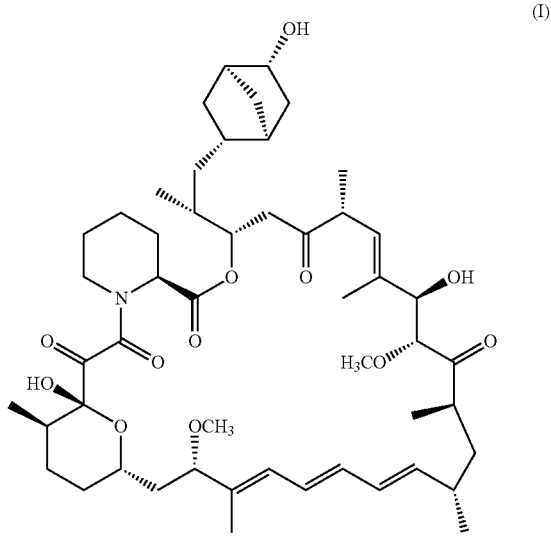

(I)

8 Claims, 4 Drawing Sheets

Rapamycin and 37R-hydroxynorbornylrapamycin

RAPAMYCIN ANALOGUE

CROSS-REFERENCE TO RELATED APPLICATIONS

This application is a 371 National Phase of PCT/GB2012/053228, filed on Dec. 21, 2012, which claims benefit of and priority to GB 1122305.4, filed on Dec. 23, 2011, which is incorporated herein by reference in its entirety for all purposes.

The present invention relates to a novel rapamycin analogue, processes for its production and its use in the therapy, especially for the treatment of lupus and/or multiple sclerosis (MS).

BACKGROUND OF THE INVENTION

Lupus is a multisystem autoimmune disease where many organs, including the kidney, can be affected. It is a chronic inflammatory disease the pathophysiology of which is manifested by the production of autoantibodies directed against multiple self-antigens, particularly those of nuclear origin. This dysregulation of the immune system results in a loss of self-tolerance, and is mediated by both T and B cells. (Reddy et al, Arthritis Research & Therapy, 2008, 10:R127; and references therein). There are very few medications approved for the treatment of lupus (Francis & Perl, 2009; Mok, 2010). These include: Prednisone (flare up and maintenance treatment), hydroxychloroquine (discoid lupus and SLE), aspirin (arthritis and pleurisy), triamcinolone hexacetonide (discoid lupus), and most recently Benlysta (SLE). In addition, several other agents are regularly prescribed including azathioprine (as a corticosteroid sparing agent), and in more aggressive regimens corticosteroids in combination with variations of cyclophosphamide, mycophenolate mofetil, or the calcineurin inhibitors such as cyclosporine and tacrolimus (Mok, 2010). For patients who are intolerant or refractory to the above listed agents, several biological agents have been utilised including intravenous immunoglobulin and the B cell depleting agent rituximab, although safety concerns have been raised about the latter through a potential link to progressive multifocal leukoencephalopathy infection.

A number of new agents are in development for the treatment of lupus. These include studies to find safer ways to use the immunosuppressive therapies described above (azathioprine, cyclophosphamide, mycophenolate mofetil), and several B cell targeting antibody therapies which exhibit potent effects but significant adverse events (for reviews see, Mok, 2010; Francis & Perl, 2009).

It has been shown that mTOR (mammalian target of rapamycin) activity is upregulated in the T cells of autoimmune patients including lupus and multiple sclerosis (MS) (Fernandez et al., 2009a,b), and that inhibition of mTORC1 by rapamycin and its analogs inhibits antigen-induced IL-2 driven T and B cell proliferation. Moreover, the activity of rapamycin and its analogues do not block proliferation of all T cell subtypes, and actually induce selective expansion of regulatory T cells (Tregs) which are important in maintaining immune self-tolerance (Donia et al., 2009; Esposito et al., 2010).

Abnormal T cell activation in SLE is linked to sustained elevation of the mitochondrial transmembrane potential, which is in turn controlled by a series of metabolic and stress related inputs (Perl et al., 2004; Fernandez et al, 2009; Fernandez & Perl, 2009). mTOR is a sensor for these inputs and as a consequence elevated mTOR signalling is observed in lupus T cells, an effect which is normalised by treatment with rapamycin (Perl et al., 2004; Fernandez et al., 2009). Moreover, two independent studies have identified a network of genes which are dysregulated in lupus/nephritis associated disease. There is a strong correlation between the abnormal transcription of these gene networks and mTOR signalling, and treatment with rapamycin returns the levels of gene transcription to asymptomatic levels. (Reddy et al., 2008; Wu et al., 2007).

Rapamycin is effective when dosed orally in preclinical mouse models of lupus. For example using the New Zealand Black White NZBW/F1 mouse model of lupus nephritis rapamycin significantly improved the clinical course of lupus nephritis (Stylianou et al., 2010; Liu et al., 2008). In the study by Liu et al (2008), treatment with rapamycin significantly decreased albuminuria, improved survival, diminished splenomegaly, preserved renal function and reduced serum anti-dsDNA antibody levels. Kidney sections from saline-treated mice revealed marked mesangial proliferation, tubular dilation with intra-tubular protein cast deposition and leukocytic infiltration of the interstitium. The rapamycin-treated mice, in contrast, had relatively mild histological changes in their kidneys. Rapamycin treatment also significantly reduced the amount of immune complex deposition in the glomeruli, suppressed the interstitial infiltration by T-cells, B-cells and macrophages as well down-regulated the intra-renal expression of RANTES. Stylianou et al (2010) found that in untreated mice, as opposed to healthy controls, Akt and mTOR were over-expressed and phosphorylated at key activating residue and rapamycin also prolonged survival, maintained normal renal function, normalized proteinuria, restored nephrin and podocin levels, reduced anti-dsDNA titres, ameliorated histological lesions, and reduced Akt and mTOR glomerular expression activation. Additional successful examples of using rapamycin in the NZBW/F1 mouse have also been published (Alperovich et al., 2007; Liu et al., 2008b). Rapamycin has also been shown to prolong survival and to reduce inflammatory changes in several organs, including the kidneys, in the MRL/lpr model of murine SLE (Warner et al., 1994).

Rapamycin has been studied in humans as part of a clinical trial of nine patients with SLE who had been treated unsuccessfully with other immunosuppressive medications (Fernandez et al., 2006). Rapamycin was well tolerated and proved effective for the reduction and control of disease activity in all 9 patients. Disease activity by BILAG (British isles Lupus Assessment Group) score and SLEDAI (SLE Disease Activity Index) and concurrent prednisone dosage at the time of rapamycin initiation and the last follow up visit (after 6-48 months of treatment) were reported. The BILAG disease flare index was reduced in 7 patients, unchanged in 1 patient, and increased in 1 patient. In the latter patient the increase in the BILAG score (which is considered to be a highly sensitive instrument for detecting disease flares) was due to transient arthralgias during the last observation period, which did not require adjustment of the prednisone dosage. At the last follow up, the mean±SEM reduction in the BILAG score in the 9 patients compared with pretreatment was 1.93±0.9 (P=0.0218). The SLEDAI was reduced by 5.3±0.8 (range 2-8) (P=0.00002). After treatment with rapamycin, the mean±SEM reduction in the daily dosage of prednisone in the 7 prescribed patients was 26.4±6.7 mg (P=0.0062). Three of the patients had cyclophosphamide-treated lupus nephritis. In all 3, the nephritis remained in remission throughout the period of rapamycin treatment, with normal serum creatinine levels and urinary protein levels of <300 mg/24 hours.

The clinical features of 7 control SLE patients not treated with rapamycin were measured. The disease activity scores of these patients were higher than those of patients who had received 6-48 months of rapamycin treatment (mean BILAG score 5.00 versus 2.11 [P=0.02]; mean SLEDAI score 3.14 versus 1.55 [P=0.11]). These observations are consistent with the notion that rapamycin treatment is beneficial in SLE. T cells from 7 healthy controls, 7 SLE controls, and 6 rapamycin-treated SLE patients were used for studies of $Ca^{2+}$ signaling and mitochondrial transmembrane potential. While mitochondrial hyperpolarization (MHP) persisted, baseline $[Ca^{2+}]_c$, and $[Ca^{2+}]_m$ and T cell activation-induced rapid $Ca^{2+}$ fluxing were normalized in rapamycin-treated patients. T cells from SLE patients not receiving rapamycin showed significantly elevated $Ca^{2+}$ levels at each time point, with P values versus levels in healthy controls ranging between 0.0008 at time 0 to 0.023 at 16 minutes. In contrast, the level of CD3/CD28-induced $Ca^{2+}$ fluxing in T cells from rapamycin-treated SLE patients was not significantly different from that in cells from healthy donors.

In summary, rapamycin has shown positive effects in murine lupus, and the findings in a human clinical study of 9 rapamycin-treated patients indicated that rapamycin can effectively control disease activity in SLE. Arthritis improved in all 9 patients, and cyclophosphamide treated nephritis in 3 patients remained in remission during rapamycin treatment. The single daily oral administration and small size of the pill was liked and well-tolerated by all patients. None of the patients discontinued the drug due to lack of efficacy or adverse effects.

Patients with lupus are at high risk of atherosclerosis (Gorman & Isenberg, 2004). Indeed, various estimates suggest that up to 30% of deaths in lupus patients may be due to coronary artery disease (Aranow & Ginzler, 2000; Petri et al., (1992); Gorman & Isenberg, 2004). It is known that rapamycin and other clinically used rapamycin analogues cause an elevation in circulating lipid/triglycerides and cholesterol levels in human patients (Morisett et al., 2002). Given the well-established link between elevated blood levels of lipid/triglycerides and cholesterol and atherosclerosis/cardiovascular disease, rapamycin analogues which are similarly effective as rapamycin as an mTOR inhibitor, but which have a significantly lesser effect on the elevation of lipid/triglycerides and cholesterol levels would be extremely useful for the treatment of lupus and other diseases in which mTOR inhibition may be effective. The range of diseases where rapamycin, or improved analogues, may be effective as pharmacological agents includes, but is not limited to, lupus, multiple sclerosis, Parkinson's disease, Huntingdon's disease, Alzheimer's disease. A recent review of neurological indications where rapamycin or rapamycin analogues may be effective treatments has been published (Bove et al., 2011).

Multiple sclerosis (MS) is a chronic autoimmune disorder of the central nervous system (CNS) that is characterized by inflammation leading to astrogliosis, demyelination, and loss of oligodendrocytes and neurons (Brinkmann et al., 2010; Compston & Coles, 2002). MS is the leading cause of neurological disability in young and middle-aged adults, affecting an estimated 2.5 million individuals worldwide (Multiple Sclerosis International Federation. Atlas of MS Database. Multiple Sclerosis International Federation website [online], http://www.atlasofms.org/index.aspx (2008)). The prevalence is greatest in Caucasians, with high prevalence rates reported in Europe, Canada, USA, Australia, New Zealand and northern Asia (Rosati, 2001; Noseworthy et al., 2000). Most patients are diagnosed between the ages of 20 and 40 years (in a 2:1 female to male ratio) (Compston & Coles, 2002). At diagnosis, ~85% of patients have relapsing-remitting MS (RRMS), which is characterized by recurrent acute exacerbations (relapses) of neurological dysfunction, followed by recovery. A substantial proportion (42-57%) of relapses may result in incomplete recovery of function and lead to permanent disability and impairment (Lublin et al., 2003). Within 6-10 years of disease onset, 30-40% of patients with RRMS have progressed to secondary progressive MS (Weinshenker et al., 1989), in which a less inflammatory and more neurodegenerative course of disease seems to take precedence. Secondary progressive MS presents with steady progression in disability, with or without superimposed relapses.

Treatment strategies for MS usually involve the management of symptoms and the use of disease-modifying drugs to reduce the frequency of relapses and to slow the progression of disability. Established first-line therapies—interferon-β (IFN-β) products and glatiramer acetate (Copaxone; Teva)—provide ~30-35% reduction in the relapse rate compared with placebo over 2 years (PRISMS Study Group, 1998; The IFNB Multiple Sclerosis Study Group, 1993; Jacobs et al., 1996; Johnson et al., 1995). IFN-β1a has also been shown to reduce the progression of disability in patients with RRMS (Goodin et al., 2002). These agents are administered by injections (with dosing schedules ranging from daily subcutaneous injections to weekly intramuscular injections), and may affect the immune system on several levels. More frequent side effects include influenza-like symptoms and injection-site reactions, which can affect tolerability and compliance (Patti, 2010). Less commonly reported adverse events for IFN-β therapies include liver dysfunction and cytopaenias (Rice, et al., 2001).

A more recently approved therapy, natalizumab (Tysabri; Elan/Biogen-Idec), is a humanized monoclonal antibody specific for the α4 subunit of the integrin α4β1 (also known as very late antigen 4) on lymphocytes (Steinman, 2005; Putzki et al., 2010). It is administered through intravenous infusions every 4 weeks and seems to offer enhanced efficacy compared with other approved products (Putzki et al., 2010). However, natalizumab has been associated with hypersensitivity reactions and with progressive multifocal leukoencephalopathy, a rare but seriously disabling or fatal infectious demyelinating disease of the brain (Steinman, 2005). Another product, the cytostatic agent mitoxantrone (for which the cellular target has not been identified), is approved for use in severe forms of relapsing MS. However, cumulative dose-related cardiac toxicity and a risk of secondary leukaemia limit the total amount that can be administered (Kingwell, et al., 2010). Because of their safety profiles, natalizumab and mitoxantrone are currently used only as second- and third-line treatments. Drugs under development for MS include the monoclonal antibodies rituximab, ocrelizumab and ofatumumab, which target CD20 to deplete B cells, as well as alemtuzumab (Campath-1H), which targets CD52 to deplete T and B cells and some monocyte-derived dendritic cells (Buttmann, 2010). Also in development are small molecules, including the oral agents cladribine (a cytotoxic adenosine deaminase-resistant purine nucleoside), fumarate (an activator of the nuclear factor E2-related factor 2 transcriptional pathway), laquinimod (the cellular target of which has not been identified), and teriflunomide (a cytostatic inhibitor of dihydroorotate dehydrogenase, which catalyses the rate-limiting step in the de novo synthesis of pyrimidines). All these agents target lymphocytes as well as other cells with the aim of inhibiting the immune-system-mediated attack on the CNS (Niino, & Sasaki, 2010). The sphingosine 1-phosphate (S1P) receptor modulator fingolimod (FTY720/Gilenya; Novartis) was the first oral treatment for RRMS approved by the US FDA (Brinkmann et al., 2010). Although the trials so far have shown fingolimod to be well tolerated, the side effects that have occurred include headache, upper respiratory tract infection, shortness of breath, diarrhea and nausea. In addition, increased levels of liver enzymes and blood pressure have been observed although these are generally mild. In the TRANSFORMS clinical trial (Trial Assessing Injectable Interferonvs. FTY720 Oral in RRMS; ClinicalTrials.gov number, NCT00340834), two deaths resulting from herpes virus infections occurred in patients taking the higher dose of fingolimod (see Garber, 2008). Other aspects of the treatments these two patients received may have contributed, but a role for fingolimod cannot be excluded given its immunomodulatory action, which could lead to an increased risk of infections.

Given the limitations of currently available therapies, the development of oral MS treatments that might offer more effective and more convenient treatment has been the focus of considerable drug discovery and development efforts in recent years.

The efficacy of rapamycin and its analogues in MS is likely attributable to a combination of their neuroprotective activity due to immunophilin/neurophilin inhibition, and the anti-inflammatory/immunosuppressive activity driven by selective mTORC1 inhibition, and remylinating properties which may be driven through both mechanisms. Rapamycin and its analogues are immunosuppressive, anti-inflammatory molecules which modulate T cell proliferation through their ability to inhibit mTOR complex 1 (mTORC1) after first binding the immunophilin FKBP12. mTOR activity is upregulated in individuals suffering from autoimmune disorders including MS and Lupus (Fernandez et al., 2009a,b), and inhibition of mTORC1 by rapamycin and its analogues inhibits antigen-induced IL-2 driven T (and B) cell proliferation. Rapamycin and its analogues do not block proliferation of all T cell subtypes, and actually induce selective expansion of regulatory T cells (Tregs) which are important in maintaining immune self-tolerance (Donia et al, 2009; Esposito et al, 2010).

Rapamycin and its analogues bind tightly to the FK506-binding protein (FKBP) family of immunophilins (Cao & Konsolaki, 2011; Gerard et al., 2011). The FKBP family consists of proteins with a variety of protein-protein interaction domains and versatile cellular functions (Kang et al., 2008). All FKBPs contain a domain with prolyl cis/trans isomerase (PPIase) activity. Binding of rapamycin or analogues to this domain inhibits their PPIase activity while mediating immune suppression through inhibition of mTOR. The larger members, FKBP51 and FKBP52, interact with Hsp90 and exhibit chaperone activity that is shown to regulate steroid hormone signalling. From these studies it is clear that FKBP proteins are expressed ubiquitously but show relatively high levels of expression in the nervous system. Consistent with this expression, FKBPs have been implicated with both neuroprotection and neurodegeneration (Cao & Konsolaki, 2011; Gerard et al., 2011; Bove et al., 2011; Kang et al., 2008). Rapamycin is a nM inhibitor of the PPIase activity of several neurophilins including FKBP12 and FKBP52, and binding to these proteins has been shown to contribute to their neuroprotective effects (Ruan et al, 2008). FKBP52 binds Tau, and Tau protein overexpression is linked to inhibition of neurite outgrowth and neuroprotection (Chambraud et al., 2010). FKBP52 controls chemotropic guidance of neural growth cones via regulation of TRPC1 channel opening (Shim et al., 2009). These data provide a link for the neurite outgrowth promoting, axonal regeneration and neuroprotective effects observed for FKBP52 knockdown/inhibition. FKBP12 has been proposed many times as the major mediator of the neuroprotective effects of immunophilins, for example FK506 protection against oxygen-glucose deprivation induced damage was not present when an anti-FKBP12 antibody was added (Labrande et al., 2006), expression of FKBP12 is increased in the brain of patients with Parkinson's Disease, Alzheimer's disease and some forms of dementia (Avramut et al., 2002). It has also been implicated as the most potent enhancer of α-synuclein aggregation (Gerard et al., 2010, Deleersnijder et al., 2011).

Rapamycin has been shown effective in preclinical experimental models of MS. For example, the effect of rapamycin administration to SJL/j mice affected by PLP139-151-induced relapsing-remitting experimental autoimmune encephalomyelitis (RR EAE) has been reported (Esposito et al., 2010). Oral or intraperitoneal treatment at the peak of disease or at the end of the first clinical attack, dramatically ameliorated the clinical course of RR-EAE. Treatment suspension resulted in early reappearance of disease. Clinical response was associated with reduced central nervous system demyelination and axonal loss. The dual action of rapamycin on both Teff and Treg cells resulted in modulation of their ratio that closely paralleled disease course. The data showed that rapamycin inhibits RR-EAE, gave evidence for the immunological mechanisms, and indicated this compound as a potential candidate for the treatment of multiple sclerosis. In a second example (Donia et al., 2009), evaluated the effects of rapamycin on the course of protracted relapsing experimental allergic encephalomyelitis (PR-EAE) in Dark Agouti (DA) rats, which serves as a preclinical model of MS. The data showed that the oral administration of rapamycin at 3 mg/kg for 28 consecutive days significantly ameliorated the course of PR-EAE in DA rats. The rats that received the medication had significantly lower clinical cumulative scores and shorter duration of the disease than did the control rats treated with the vehicle.

The clinical utility in MS of rapamycin has been shown directly, but its close analogue and mTOR inhibitor temsirolimus has been studied up to Phase 2B, where the efficacy and safety of temsirolimus was evaluated in patients with clinically definite relapsing-remitting MS (RRMS) or secondary progressive MS with relapses (Kappos et al., 2005; Moraal et al., 2010). It was a multicentre, randomized, double-blind, placebo-controlled, phase 2 clinical trial conducted in 296 patients aged 19-57 years. Patients received oral temsirolimus (2, 4, or 8 mg,) 1×daily, or placebo, for 9 months. The primary end point was the cumulative number of new Gd-enhanced T1 lesions at 9 months on MRI. Total brain volume, number of relapses, mean EDSS scores, other MRI measures and health outcomes were secondary end-points.

Patients receiving 8 mg temsirolimus achieved significant reductions (47.8%) in the cumulative number of new Gd-enhancing T1 lesions on MRI compared with placebo (p=0.010). MRI endpoints showed a dose response, the 8 mg dose reaching statistical significance for the primary endpoint by 32 weeks (p=0.024). Brain volume data suggested a decrease in brain volume atrophy at 36 weeks in the 8 mg group compared with placebo. The 8 mg group showed a 51% reduction in number of relapses per patient vs. placebo (p=0.023). Dose-related trends in percentage of relapse-free patients and progression of disability were also noted. Serious adverse events occurred at similar frequencies across all treatment groups. Aphthous stomatitis/mouth ulceration, hyperlipidaemia, rashes, and menstrual dysfunction were reported more often in the 8 mg group vs. placebo. It was concluded that an oral, 8 mg dose of temsirolimus administered over 9 months in patients with relapsing forms of MS resulted in significant beneficial effects on the incidence of new enhancing MRI lesions and number of relapses, with an acceptable risk/benefit profile.

Rapamycin (sirolimus) (FIG. 4) is a lipophilic macrolide produced by *Streptomyces hygroscopicus* NRRL 5491 (Sehgal et al., 1975; Vezina et al., 1975; U.S. Pat. No. 3,929,992; U.S. Pat. No. 3,993,749) with a 1,2,3-tricarbonyl moiety linked to a pipecolic acid lactone (Paiva et al., 1991). For the purpose of this invention rapamycin is described by the numbering convention of McAlpine et al. (1991) in preference to the numbering conventions of Findlay et al. (1980) or Chemical Abstracts (11$^{th}$ Cumulative Index, 1982-1986 p60719CS).

Rapamycin has significant therapeutic value due to its wide spectrum of biological activities (Huang et al, 2003). The compound is a potent inhibitor of the mammalian target of rapamycin (mTOR), a serine-threonine kinase downstream of the phosphatidylinositol 3-kinase (PI3K)/Akt (protein kinase B) signalling pathway that mediates cell survival and proliferation. This inhibitory activity is gained after rapamycin binds to the immunophilin FK506 binding protein 12 (FKBP12) (Dumont, F. J. and Q. X. Su, 1995). In T cells rapamycin inhibits signalling from the IL-2 receptor and subsequent autoproliferation of the T cells resulting in immunosuppression. Rapamycin is marketed as an immunosuppressant for the treatment of organ transplant patients to prevent graft rejection (Huang et al, 2003). In addition to immunosuppression, rapamycin has found therapeutic application in cancer (Vignot et al, 2005), and has potential therapeutic use in the treatment of a number of diseases, for example, cancer, cardiovascular diseases such as restenosis, autoimmune diseases such as multiple sclerosis and lupus, rheumatoid arthritis, fungal infection and neurodegenerative diseases such as Alzheimer's disease, Parkinson's disease and Huntington's disease.

Despite its utility in a variety of disease states rapamycin has a number of major drawbacks. The most serious adverse event associated with its use is hyperlipidemia. This can lead to dose reduction and treatment withdrawal. In particular, any potential this class has in SLE is limited due to the naturally high lipid levels in these patients (Aranow & Ginzler, 2000; Petri et al., (1992); Gorman & Isenberg, 2004). It is also a substrate of cell membrane efflux pump P-glycoprotein (P-gp; LaPlante et al, 2002, Crowe et al, 1999) which pumps the compound out of the cell making the penetration of cell membranes by rapamycin poor. This causes poor absorption of the compound after dosing. In addition, since a major mechanism of multi-drug resistance of cancer cells is via cell membrane efflux pump, rapamycin is less effective against multi-drug resistance (MDR) cancer cells. Rapamycin is also extensively metabolised by cytochrome P450 enzymes (Lampen et al, 1998). Its loss at hepatic first pass is high, which contributes further to its low oral bioavailability. The role of CYP3A4 and P-gp in the low bioavailability of rapamycin has been confirmed in studies demonstrating that administration of CYP3A4 and/or P-gp inhibitors decreased the efflux of rapamycin from CYP3A4-transfected Caco-2 cells (Cummins et al, 2004) and that administration of CYP3A4 inhibitors decreased the small intestinal metabolism of rapamycin (Lampen et al, 1998). The low oral bioavailability of rapamycin causes significant inter-individual variability resulting in inconsistent therapeutic outcome and difficulty in clinical management (Kuhn et al, 2001, Crowe et al, 1999).

Therefore, there is a need for the development of novel rapamycin-like compounds that have reduced side effects, including hyperlipidaemia, are not substrates of P-gp, and that may be metabolically more stable and therefore may have improved bioavailability.

A range of synthesised rapamycin analogues using the chemically available sites of the molecule has been reported. The description of the following compounds was adapted to the numbering system of the rapamycin molecule described in FIG. 4. Chemically available sites on the molecule for derivatisation or replacement include C40 and C28 hydroxyl groups (e.g. U.S. Pat. No. 5,665,772; U.S. Pat. No. 5,362,718), C39 and C16 methoxy groups (e.g. WO 96/41807; U.S. Pat. No. 5,728,710), C32, C26 and C9 keto groups (e.g. U.S. Pat. No. 5,378,836; U.S. Pat. No. 5,138,051; U.S. Pat. No. 5,665,772). Hydrogenation at C17, C19 and/or C21, targeting the triene, resulted in retention of antifungal activity but relative loss of immunosuppression (e.g. U.S. Pat. No. 5,391,730; U.S. Pat. No. 5,023,262). Significant improvements in the stability of the molecule (e.g. formation of oximes at C32, C40 and/or C28, U.S. Pat. No. 5,563,145, U.S. Pat. No. 5,446,048), resistance to metabolic attack (e.g. U.S. Pat. No. 5,912,253), bioavailability (e.g. U.S. Pat. No. 5,221,670; U.S. Pat. No. 5,955,457; WO 98/04279) and the production of prodrugs (e.g. U.S. Pat. No. 6,015,815; U.S. Pat. No. 5,432,183) have been achieved through derivatisation.

An object of the invention is to identify a further derivative of rapamycin which retains its beneficial effects in therapy without some or all of its side effects. In addition, it is advantageous to have a molecule that has more potent FKBP12 inhibition.

SUMMARY OF THE INVENTION

In a first aspect, the present invention provides a novel rapamycin analogue, defined by formula (I) below,

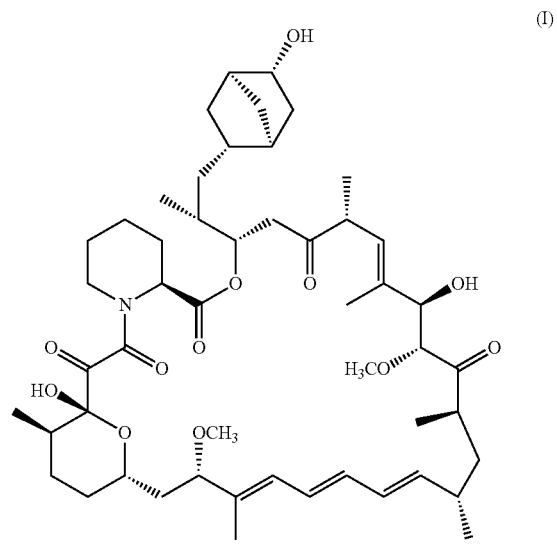 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2C[C@@H]3C[C@H]2C[C@H]3O)CC(=O)[C@H](C)/C=C(\C)[C@@H](O)[C@@H](OC)C(=O)[C@H](C)C[C@H](C)/C=C/C=C/C=C/1C]

or a pharmaceutically acceptable salt thereof.

The compound of formula (I) (and any pharmaceutically acceptable salt thereof) is referred to hereinafter as "compound of the invention" or by its generic name "37R-hydroxynorbornylrapamycin".

DEFINITIONS

The articles "a" and "an" are used herein to refer to one or to more than one (i.e. at least one) of the grammatical objects of the article. By way of example "an analogue" means one analogue or more than one analogue.

As used herein, the term "lupus" includes, without limitation: systemic lupus erythrematosis (SLE), lupus nephritis, acute cutaneous lupus erythematosus, subacute cutaneous lupus erythematosus, chronic cutaneous lupus erythematosus, drug-induced lupus erythematosus, neonatal lupus erythematosus, As used herein, the terms "multiple sclerosis" or "MS" include, without limitation: relapsing remitting, secondary progressive and primary progressive multiple sclerosis.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Trepanier et al, 1998, Gallant-Haidner et al, 2000).

As used herein, the term "in substantially pure form" means that the compound is provided in a form which is substantially free of other compounds (particularly polyketides or other rapamycin analogues) produced in fermentation processes, especially a fermentation process involving feeding starter acid of formula (II) (see infra) to a rapamycin producing strain that has been genetically altered to remove or inactivate the rapK gene or homologue thereof. For example the purity of the compound is at least 90%, for example at least 95%, for example at least 98% especially at least 99% as regards the polyketide content of the form in which is it presented. Hence both prior and post formulation as a pharmaceutical product the compound of the invention suitably represents at least 90%, for example at least 95%, for example at least 98% for example at least 99% of the polyketide content.

The pharmaceutically acceptable salts of the compound of the invention include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The invention embraces solvates of 37R-hydroxynorbornylrapamycin, or a pharmaceutically acceptable salt thereof. Examples of solvates include hydrates.

References hereinafter to a compound according to the invention include both 37R-hydroxynorbornylrapamycin and its pharmaceutically acceptable salts (and any solvates thereof).

DESCRIPTION OF THE INVENTION

The compound of the invention, in spite of its structural relatedness to rapamycin, shows a surprisingly different pharmacological profile. In particular, in comparison with rapamycin or certain known analogues, it shows shorter half life and significantly reduced lipid levels after repeated dosing, and is expected to display higher bioavailability, increased cell membrane permeability and decreased efflux in comparison with rapamycin, and may be less of a substrate for P-gp.

Thus the advantageous properties of the compound of the invention include:
  good inhibition of mTOR (as measured by inhibition of phosphorylation of S6 Kinase) with potency which is similar or greater than rapamycin and other analogues (see Example 3);
  lower half life as compared with rapamycin (based on studies in rats, see Example 4); and
  reduced incidence of hyperlipidaemia following repeated oral dosage at levels required for similar efficacy to the rapamycin analogue CCI-779 (based on studies in mice, see Example 5).
  more potent inhibition of FKBP12 than rapamycin, leading to an increased neuroprotective effect In treatment of diseases such as lupus and MS the short half life is expected to lead to improved therapeutic index because the side effects that result from longer exposure (such as hyperlipidaemia) are expected to be significantly reduced.

The compound of the invention may be produced as a direct fermentation product, by feeding a starter acid of formula (II)

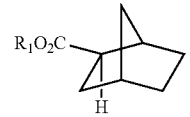

wherein $R_1$ represents H, or an alkyl group, such as a C1-6alkyl group e.g. methyl or ethyl to a rapamycin producing strain that has been genetically altered to remove or inactivate the rapK gene or homologue thereof.

By "homologue" in this context is meant a gene whose product is a chorismatase with function equivalent to that of the rapK gene product RapK (Andexer et al., 2011).

Suitable conditions for such a process are described in WO04/007709 and WO06/016167, the contents of which are incorporated by reference in their entirety. Specifically, a mutant strain of the rapamycin producing organism, *Streptomyces hygroscopicus*, was generated which lacks the rapK gene and is called *S. hygroscopicus* ΔrapK (BIOT-4010; see Example 1). Other suitable production strains include *S. hygroscopicus* MG2-10 (pLL178), a derivative of *S. hygroscopicus* NRRL5491. The generation of *S. hygroscopicus* MG2-10 is described in example 2 of WO04/007709, and to generate a suitable production strain, this should be complemented with rapIJMNOQL, using an expression plasmid such pLL178 (as described in example 7 of WO06/016167). Fermentation of BIOT-4010, or a similar strain, such as *S. hygroscopicus* MG2-10 (pLL178) (WO04/007709, WO06/016167) in a suitable medium, such as but not limited to MD6, at a suitable temperature, such as 26° C., with addition of exogenous feed, e.g. (1R*,2R*,4S*)-bicyclo[2.2.1]heptane-2-carboxylic acid, typically at 24 hours is then sufficient for the production of the compound of the invention, 37R-hydroxynorbornylrapamycin (see Example 2). Peak titers are observed between 3 and 8 days from inoculation. The acid form of compound of formula (II) is (1R,2R,4S)-bicyclo[2.2.1]heptane-2-carboxylic acid.

Rapamycin producing strains include *Streptomyces hygroscopicus, Actinoplates* sp. N902-109 (see Nishida et al (1995)) and *Streptomyces* sp. A 91-261402 (see WO94/18207). Other rapamycin producing strains are mentioned in WO95/06649. The contents of the aforementioned two patent applications are herein incorporated by reference in their entirety.

The present invention also provides the compound of the invention in substantially pure form. The compound of the invention may be purified e.g. from other fermentation components (including other polyketide components) by conventional separation techniques such as flash chromatography, preparative HPLC and/or crystallisation.

Hence, a process for preparing a compound of the invention in substantially pure form comprises the steps of (i) feeding a starter acid of formula (II)

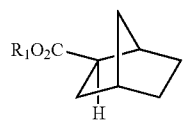

wherein $R_1$ represents H or an alkyl group,
to a rapamycin producing strain that has been genetically altered to remove or inactivate the rapK gene or homologue thereof; and (ii) isolating and purifying the compound of the invention.

The present invention provides the compound of the invention for use as a pharmaceutical, in particular in the treatment of lupus and/or multiple sclerosis (MS). In a specific embodiment, the present invention provides for the use of the compound of the invention in the treatment of lupus).

The present invention also provides a method of treatment of lupus and/or multiple sclerosis (MS) which comprises administering to a subject in need thereof an effective amount of the compound of the invention.

The present invention also provides the use of the compound of the invention for the manufacture of a medicament for the treatment of lupus and/or multiple sclerosis (MS).

The compound of the invention may also be useful in the induction or maintenance of immunosuppression, the stimulation of neuronal regeneration or the treatment of fungal infections, transplantation rejection, graft vs. host disease, autoimmune disorders, diseases of inflammation vascular disease or fibrotic diseases.

The present invention also provides a pharmaceutical composition comprising the compound of the invention together with one or more pharmaceutically acceptable diluents or carriers.

An aspect of the invention is a pharmaceutical composition comprising the compound of formula (I) as defined above, or a pharmaceutically acceptable salt thereof, together with one or more pharmaceutically acceptable diluents or carriers wherein the compound of formula (I) is present in the composition in an amount of at least 95%, for example at least 98% especially at least 99% of the polyketide content of the composition.

The compound of the invention or a formulation thereof may be administered by any conventional method for example but without limitation it may be administered parenterally, orally, topically (including buccal, sublingual or transdermal), via a medical device (e.g. a stent), by inhalation or via injection (subcutaneous or intramuscular). The treatment may consist of a single dose or a plurality of doses over a period of time.

Whilst it is possible for the compound of the invention to be administered alone, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The compound of the invention may be administered alone or in combination with other therapeutic agents, co-administration of two (or more) agents allows for significantly lower doses of each to be used, thereby reducing the side effects seen. Therefore in one embodiment, the compound of the invention is co-administered with another therapeutic agent for the treatment of lupus, for which preferred agents include, but are not limited to: NSAIDs—e.g. naproxen, ibuprofen; antimalarials—hydroxychloroquine, chloroquine, quinacrine; corticosteroids—e.g prednisone, prednisolone, medrol; immunosuppressives—azathioprine, methotrexate, cyclophosphamide, mycophenylate mofetil, cyclosporine; others—e.g. dapsone, rituximab, belimumab In one embodiment, the compound of the invention is co-administered with another therapeutic agent for the treatment of MS; preferred agents include, but are not limited to, Interferon beta-1b, Interferon beta-1a, glatiramer, mitoxantrone, cyclophosphamide and corticosteroids (e.g. methylprednisolone, prednisone, dexamethasone). Further therapeutic agents for the treatment of MS include fingolimod, natalizumab, alemtuzumab, dimethyl fumarate and teriflunomide, By co-administration is included any means of delivering two or more therapeutic agents to the patient as part of the same treatment regime, as will be apparent to the skilled person. Whilst the two or more agents may be administered simultaneously in a single formulation this is not essential. The agents may be administered in different formulations and at different times.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compound of the invention will normally be administered intravenously, orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

For example, the compound of the invention can be administered orally, buccally or sublingually in the form of tablets, capsules, ovules, elixirs, solutions or suspensions, which may contain flavouring or colouring agents, for immediate-, delayed- or controlled-release applications.

Solutions or suspensions of the compound of the invention suitable for oral administration may also contain excipients e.g. N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate), Such tablets may contain excipients such as microcrystalline cellulose, lactose (e.g. lactose monohydrate or lactose anyhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxypropylcellulose (HPC), macrogol 8000, sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oeyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

The compound of the invention may also be administered using medical devices known in the art. For example, in one embodiment, a pharmaceutical composition of the invention can be administered with a needleless hypodermic injection device, such as the devices disclosed in U.S. Pat. No. 5,399, 163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. In a specific embodiment a hydroxynorbornylrapamycin analogue may be administered using a drug-eluting stent, for example one corresponding to those described in WO 01/87263 and related publications or those described by Perin (Perin, E C, 2005). Many other such implants, delivery systems, and modules are known to those skilled in the art.

The dosage to be administered of a compound of the invention will vary according to the particular compound, the disease involved, the subject, and the nature and severity of the disease and the physical condition of the subject, and the selected route of administration. The appropriate dosage can be readily determined by a person skilled in the art. For example, without limitation, a dose of up to 15 mg daily e.g. 0.1 to 15 mg daily (or a higher dose given less frequently) may be contemplated.

The compositions may contain from 0.1%, e.g. from 0.1-70%, preferably from 5-60%, more preferably from 10-30%, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

All % values mentioned herein are % w/w unless the context requires otherwise.

GENERAL METHODS

Figure 1:
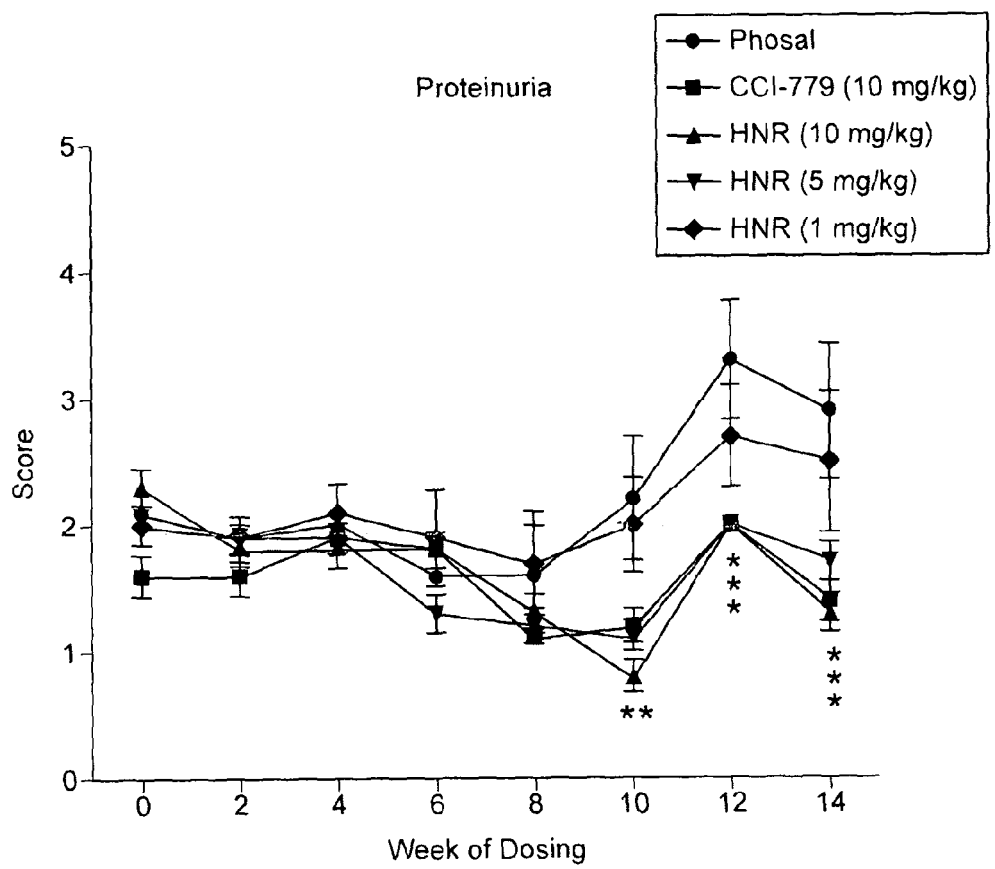
FIG. 1: Effect of 37R-hydroxynorbornylrapamycin on development of proteinuria in NZBWF1 lupus model (see Example 5)

A person of skill in the art will be able to determine the pharmacokinetics and bioavailability of the compound of the invention using in vivo and in vitro methods known to a person of skill in the art, including but not limited to those described below and in Gallant-Haidner et al, 2000 and Trepanier et al, 1998 and references therein. The bioavailability of a compound is determined by a number of factors, (e.g. water solubility, cell membrane permeability, the extent of protein binding and metabolism and stability) each of which may be determined by in vitro tests as described in the examples herein, it will be appreciated by a person of skill in the art that an improvement in one or more of these factors will lead to an improvement in the bioavailability of a compound. Alternatively, the bioavailability of the compound of the invention may be measured using in vivo methods as described in more detail below, or in the examples herein.

In order to measure bioavailability in vivo, a compound may be administered to a test animal (e.g. mouse or rat) both intraperitoneally (i.p.) or intravenously (i.v.) and orally (p.o.) and blood samples are taken at regular intervals to examine how the plasma concentration of the drug varies over time. The time course of plasma concentration over time can be used to calculate the absolute bioavailability of the compound as a percentage using standard models. An example of a typical protocol is described below.

For example, mice or rats are dosed with 1 or 3 mg/kg of the compound of the invention i.v. or 1, 5 or 10 mg/kg of the compound of the invention p.o. Blood samples are taken at 5 min, 15 min, 1 h, 4 h and 24 h intervals, and the concentration of the compound of the invention in the sample is determined via LCMS-MS. The time-course of plasma or whole blood concentrations can then be used to derive key parameters such as the area under the plasma or blood concentration-time curve (AUC—which is directly proportional to the total amount of unchanged drug that reaches the systemic circulation), the maximum (peak) plasma or blood drug concentration, the time at which maximum plasma or blood drug concentration occurs (peak time), additional factors which are used in the accurate determination of bioavailability include: the compound's terminal half-life, total body clearance, steady-state volume of distribution and F %. These parameters are then analysed by non-compartmental or compartmental methods to give a calculated percentage bioavailability, for an example of this type of method see Gallant-Haidner et al, 2000 and Trepanier et al, 1998, and references therein.

The efficacy of the compound of the invention may be tested in in vivo models for neurodegenerative diseases which are described herein and which are known to a person of skill in the art. Such models include, but are not limited to, for Alzheimer's disease—animals that express human familial Alzheimer's disease (FAD) p-amyloid precursor (APP), animals that overexpress human wild-type APP, animals that overexpress p-amyloid 1-42(pA), animals that express FAD presenillin-1 (PS-1) (e. g. German and Eisch, 2004). For multiple sclerosis—the experimental autoimmune encephalomyelitis (EAE) model (see Bradl, 2003). For Parkinson's disease—the 1-methyl-4-phenyl-1,2,3,6-tetrahydropyridine (MPTP) model or the 6-hydroxydopamine (6-OHDA) model (see e.g. Emborg, 2004; Schober A. 2004). For Huntington's disease there are several models including the R6 lines model generated by the introduction of exon 1 of the human Huntington's disease (HD) gene carrying highly expanded CAG repeats into the mouse germ line (Sathasivam et al, 1999) and others (see Hersch and Ferrante, 2004).

Materials & Methods

Materials

Unless otherwise indicated, all reagents used in the examples below were obtained from commercial sources.

(1R*,2R*,4S*)-bicyclo[2.2.1]heptane-2-carboxylic acid, i.e. (±)2-exo-norbornanecarboxylic acid was prepared by the method of Gu et al, 2011

(1R,2R,4S)-bicyclo[2.2.1]heptane-2-carboxylic acid was prepared by the method of Avenoza et al, 1992.

(1R,2S,4S)-bicyclo[2.2.1]heptane-2-carboxylic acid was prepared by the method of Avenoza et al, 1992.

Culture

*S. hygroscopicus* BIOT-4010 or MG2-10 was maintained on medium 1 agar plates (see below) at 28° C. Spore stocks were prepared after growth on medium 1, preserved in 20% w/v glycerol:10% w/v lactose in distilled water and stored at −80° C. Vegetative cultures were prepared by inoculating 0.1 mL of frozen stock into 50 mL medium 2 (see below) in 250 mL flask. The culture was incubated for 36 to 48 hours at 28° C., 300 rpm.

Production Method

Vegetative cultures were inoculated at 2.5-5% v/v into medium 3. Cultivation was carried out for 6-7 days, 26° C., 300 rpm.

Feeding Procedure

The feeding/addition of (1R,2R,4S)-bicyclo[2.2.1]heptane-2-carboxylic acid, (1R,2S,4S)-bicyclo[2.2.1]heptane-2-carboxylic acid or (1R*,2R*,4S*)-bicyclo[2.2.1]heptane-2-carboxylic acid (also known as (±)2-exo-norbornanecarboxylic acid) was carried out 24-48 hours after inoculation and was fed at 1-2 mM final concentration unless stated otherwise.

Medium 1:

| component | Source | Catalogue # | Per L |
|---|---|---|---|
| Corn steep powder | Sigma | C-8160 | 2.5 g |
| Yeast extract | Difco | 0127-17 | 3 g |
| Calcium carbonate | Sigma | C5929 | 3 g |
| Iron sulphate | Sigma | F8633 | 0.3 g |
| BACTO agar | | | 20 g |
| Wheat starch | Sigma | S2760 | 10 g |
| Water to | | | 1 L |

The media was then sterilised by autoclaving 121° C., 20 min.

MD6 Medium (Small Scale Fermentation Medium)

| Component | Per L |
|---|---|
| Toasted Nutrisoy (ADM Ingredients Ltd) | 30 g |
| Corn starch (Sigma) | 30 g |
| Avedex W80 dextrin (Deymer Ingredients Ltd) | 19 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |
| NaCl | 5 g |
| $CaCO_3$ (Caltec) | 10 g |
| $MnCl_2 \cdot 4H_2O$ | 10 mg |
| $MgSO_4 \cdot 7H_2O$ | 2.5 mg |
| $FeSO_4 \cdot 7H_2O$ | 120 mg |
| $ZnSO_4 \cdot 7H_2O$ | 50 mg |
| MES (2-morpholinoethane sulphuric acid monohydrate) | 21.2 g |
| pH is corrected to 6.0 with 1M NaOH | |

Before sterilization 0.4 mL of Sigma α-amylase (BAN 250) was added to 1 L of medium.

Medium was sterilised for 20 min at 121° C.

After sterilisation 0.35 mL of sterile 40% fructose and 0.10 mL of L-lysine (140 mg/mL in water, filter-sterilised) was added to each 7 mL.

RapV7 Seed Medium

| Component | Per L |
|---|---|
| Toasted Nutrisoy (ADM Ingredients Ltd) | 5 g |
| Avedex W80 dextrin (Deymer Ingredients Ltd) | 35 g |
| Corn Steep Solids (Sigma) | 4 g |
| $(NH_4)_2SO_4$ | 2 g |
| Lactic acid (80%) | 1.6 mL |
| $CaCO_3$ (Caltec) | 7 g |
| Adjust pH to 7.5 with 1M NaOH. | |

The media was then sterilised by autoclaving 121° C., 20 min. d-Glucose (to 10 g/L) was added after autoclaving.

MD6 Medium (Small Scale Fermentation Medium)

| Component | Per L |
|---|---|
| Toasted Nutrisoy (ADM Ingredients Ltd) | 30 g |
| Avedex W80 dextrin (Deymer Ingredients Ltd) | 19 g |
| Corn starch | 30 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |

-continued

| Component | Per L |
|---|---|
| NaCl | 5 g |
| $CaCO_3$ (Caltec) | 10 g |
| $MnCl_2 \cdot 4H_2O$ | 10 mg |
| $MgSO_4 \cdot 7H_2O$ | 2.5 mg |
| $FeSO_4 \cdot 7H_2O$ | 120 mg |
| $ZnSO_4 \cdot 7H_2O$ | 50 mg |
| MES | 21.2 g |

Medium was adjusted to pH6.0, 0.4 mL/L alpha-amylase (Sigma A7595—liquid, >250 units/g) added and the media sterilised for 30 min at 121° C. d-Fructose (to 20 g/L) and l-lysine (monohydrochloride) (to 2 g/L) were added after autoclaving.

MD6/5-1 Medium (Medium Scale Fermentation Medium)

| Component | Per L |
|---|---|
| Toasted Nutrisoy (ADM Ingredients Ltd) | 15 g |
| Avedex W80 dextrin (Deymer Ingredients Ltd) | 50 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |
| NaCl | 13 g |
| $CaCO_3$ (Caltec) | 10 g |
| $MnCl_2 \cdot 4H_2O$ | 3.5 mg |
| $MgSO_4 \cdot 7H_2O$ | 15 mg |
| $FeSO_4 \cdot 7H_2O$ | 150 mg |
| $ZnSO_4 \cdot 7H_2O$ | 60 mg |
| SAG 471 | 0.5 ml |

Medium was sterilised for 30 min at 121° C.
After sterilisation 15 g of Fructose per L was added.
After 48 h 0.5 g/L of L-lysine was added.

Analytical Methods

Method A

Injection volume: 0.005-0.1 mL (as required depending on sensitivity). HPLC was performed on Agilent "Spherisorb" "Rapid Resolution" cartridges SB C8, 3 micron, 30 mm×2.1 mm, running a mobile phase of:

Mobile phase A: 0.01% Formic acid in pure water
Mobile phase B: 0.01% Formic acid in Acetonitrile
Flow rate: 1 mL/minute.

Linear gradient was used, from 5% B at 0 min to 95% B at 2.5 min holding at 95% B until 4 min returning to 5% B until next cycle. Detection was by UV absorbance at 254 nm and/or by mass spectrometry electrospray ionisation (positive or negative) using a Micromasss Quattro-Micro instrument.

Method B

Injection volume: 0.02 mL. HPLC was performed on 3 micron BDS C18 Hypersil (ThermoHypersil-Keystone Ltd) column, 150×4.6 mm, maintained at 50° C., running a mobile phase of:

Mobile phase A: Acetonitrile (100 mL), trifluoroacetic acid (1 mL), 1 M ammonium acetate (10 mL) made up to 1 L with deionised water.
Mobile phase B: Deionised water (100 mL), trifluoroacetic acid (1 mL), 1M ammonium acetate (10 mL) made up to 1 L with acetonitrile.
Flow rate: 1 mL/minute.

A linear gradient from 55% B-95% B was used over 10 minutes, followed by 2 minutes at 95% B, 0.5 minutes to 55% B and a further 2.5 minutes at 55% B. Compound detection was by UV absorbance at 280 nm.

Method C

The HPLC system comprised an Agilent HP1100 and was performed on 3 micron BDS C18 Hypersil (ThermoHypersil-Keystone Ltd) column, 150×4.6 mm, maintained at 40° C., running a mobile phase of:
Mobile phase A: deionised water.
Mobile phase B: acetonitrile.
Flow rate: 1 mL/minute.

This system was coupled to a Bruker Daltonics Esquire3000 electrospray mass spectrometer. Positive negative switching was used over a scan range of 500 to 1000 Dalton.

A linear gradient from 55% B-95% B was used over 10 minutes, followed by 2 minutes at 95% B, 0.5 minutes to 55% B and a further 2.5 minutes at 55% B.

Method D

Injection volume: 0.025 mL. HPLC was performed on 3 micron Gemini NX C18 (Phenomenex) column, 150×4.6 mm, maintained at 50° C., running a mobile phase of:
Mobile phase A: deionised water with formic acid (0.1%)
Mobile phase B: acetonitrile with formic acid (0.1%)
Flow rate: 1 mL/minute.

A linear gradient from 55% B-95% B was used over 10 minutes, followed by 2 minutes at 95% B, 0.5 minutes to 55% B and a further 2.5 minutes at 55% B. Compound detection was by UV absorbance at 280 nm.

Method E
Mobile Phase A 10 mM Ammonium Acetate/Water
Mobile Phase B ACN
Column FluoroSep-RP Phenyl HS, 50×2.1 mm, 5 μm
Column temperature Ambient
Autosampler needle washing soln 0.5% Formic Acid in 10% ACN/Water
Injection volume 0.012 ml
Autosampler temperature 10° C.
WYE-126657 retention time 3.8 min.
IS (WAY-130779) retention time 3.8 min.
Total run time 6.7 min.

GRADIENT PROGRAM

| Total Time (min) | Flow Rate (mL/min) | Mobile Phase A (%) | Mobile Phase B (%) | Gradient Profile |
|---|---|---|---|---|
| 0.0 | 0.6 | 90 | 10 | 1.0 |
| 1.5 | 0.6 | 90 | 10 | 1.0 |
| 3.5 | 0.6 | 10 | 90 | 1.0 |
| 5.0 | 0.6 | 10 | 90 | 1.0 |
| 5.2 | 0.6 | 90 | 10 | 1.0 |
| 6.7 | 0.6 | 90 | 10 | 1.0 |

Mass Spectrometry Conditions
Sciex API 4000 (Serial No.: V09300509) Batman
Experiment: MRM (multiple reaction monitoring)

| Ion Source | Curtain | CAD | GS1 | GS2 | IS | Temp (° C.) | Ihe | EP |
|---|---|---|---|---|---|---|---|---|
| Turbo Spray | 25 | 4 | 50 | 50 | +5000 | 500 | on | 10 |

| Compound | MS/MS Transition* | MRM | Dwell (msec) | DP | CE | CXP |
|---|---|---|---|---|---|---|
| 37R-hydroxynorbornylrapamycin | 913.7 > 864.6 | —NH$_3$CH$_3$OH | 250 | 76 | 17 | 18 |
| temsirolimus (IS) | 1047.6 > 980.6 | —NH$_3$—CH$_3$OH—H$_2$O | 250 | 91 | 29 | 20 |
| Phosphatidylcholine (matrix effect) | 184 > 184 | | 250 | 150 | 7 | 5 |

(M + NH$_4$)$^+$ is parent ion.

EXAMPLES

Example 1

Generation of *S. hygroscopicus* BIOT-4010 or MG2-10

For methodology to generate *S. hygroscopicus* MG2-10, refer to example 2 in WO2004/007709. This strain can be used in place of BIOT-4010 to generate 37R-hydroxynorbornylrapamycin, following transformation, using standard protocols, with a vector expressing rapIJMNOL, such as pLL158 (WO2006/016167, Gregory et al., 2012).

BIOT-3410 is a higher-producing derivative of the rapamycin-producing strain of *S. hygroscopicus* NRRL5491, generated by mutagenesis and selection of higher producing variants and BIOT-4010 is a mutant of BIOT-3410 in which rapK has been specifically deleted, using similar methodology to that described for *S. hygroscopicus* MG2-10. BIOT-4010 is therefore a higher producing variant of *S. hygroscopicus* MG2-10, based on the selected strain. However, *S. hygroscopicus* NRRL5491 itself, or a derivative, could be used to generate a strain able to produce compounds of the invention.

Our strategy took advantage of a naturally occurring Mfel site close to the 5'-end of rapK. To generate upstream and downstream areas of homology for integration, the 7.3 kbp Ncol fragment from pR 19 (Schwecke et al., 1995) was cloned into plitmus28 that had been digested with Ncol and dephosphorylated, and the 4.2 kbp Nhei/Pstl fragment from cosmid-2 (Schwecke et al., 1995) was cloned into plitmus28 digested with Psti-Spel. This gave intermediate plasmids plitmus28-7.3 and plitmus28-4.2 respectively. To introduce the desired deletion from the Mfel site to an internal site of rapK two oligonucleotides were used to amplify the required region, BioSG159: 5'-CCCCAATTGGTGTCGCTC-GAGAACATCGCCCGGGTGA-3' (SEQ ID NO:1) and BioSG 158: 5'-CGCCGCAAGTAGCACCGCTCGGCGAA-GATCTCCTGG-3' (SEQ ID NO:2) using plasmid pR 19 as template (Schwecke 1995). The resulting 1.5 kbp PCR product was treated with T4 polynucleotide kinase and cloned into plitmus28 that had been digested with EcoRV and dephosphorylated, and the cloned PCR product was sequenced. The 1.5 kbp Mfei-Bg/11 fragment from this plasmid was excised and used to replace the 2.3 kbp Mfei-Bg/11 fragment of plitmus28-4.2. To complete the construct the 3.3 kbp Mfei-HindIII fragment of this plasmid was ligated into similarly digested plitmus28-7.3. Finally, the deletion construct was transferred into the conjugative *Streptomyces* vector pKC 1132 (Bierman et al., 1992) as a Hindiii/Xbal fragment. The final construct was designated pSG3998.

Plasmid pSG3998 was transformed by electroporation into *E. coli* ET12567:pUZ8002 and selected on 2TY plates containing apramycin (50 ug/mL), kanamycin (25 ug/mL) and chloroamphenicol (12.5 ug/mL) which were incubated at 30° C. overnight. Colonies were used to inoculate liquid 2TY media (4 mL) containing the same antibiotics and incubated overnight at 30° C. and 250 rpm. Approximately 0.8 mL of overnight culture was used to inoculate 2TY (10 mL) containing the same antibiotics and incubated at 30° C. and 250 rpm until they reached an OD-0.5 (595 nm). Cultures were centrifuged at 4000 rpm, washed twice with 2TY and the resulting cell pellet was resuspended in 2TY (0.25 mL). Spores of BIOT-3401 were thawed and pelleted by centrifugation (4000 rpm) and washed with 2TY (1 mL) before suspending in 2TY (1 mL). Spores were then exposed to heat shock at 50° C. for 10 min before placing immediately on ice. Approximately 100 uL spore stock was used per conjugation, and 2TY (150 uL) was added to adjust the volume to 0.25 mL. Conjugations were performed by mixing 0.25 mL of the washed E. coli cells with the adjusted BIOT-3401 spore stock and spreading immediately on a dried R6 plate. Plates were dried briefly, wrapped in clingfilm and incubated at 37° C. for 2-3 h. Each plate was then overlaid with sterile water (1 mL) containing nalidixic acid (15 uL of a 50 mg/L solution), dried and incubated at 37° C. overnight. The plates were then overlaid with sterile water (1 mL) containing apramycin (15 uL of a 100 mg/L solution) and incubated at 37° C. Ex-conjugate colonies appeared after 4-7 days and were picked onto Medium 1 plates containing apramycin (50 ug/mL) and nalidixic acid (25 ug/mL), and incubated at 37° C. for 3-4 days before re-patching to Medium 1 plates containing apramycin (50 ug/mL) and nalidixic acid (25 ug/mL). This patching process was then repeated for three rounds on Medium 1 plates with no antibiotics, incubating at 37° C. until good growth was visible. The patches were then transferred to Medium 1 plates and incubated at 28° C. to encourage sporulation (~7-10 days). Spores were harvested, filtered through cotton wool and dilution series prepared. Aliquots (100 uL) of the dilution series were plated onto Medium 1 plates and incubated at 28° C. until spores were visible on the colonies. Colonies were patched in parallel to plates with and without apramycin (50 ug/mL). Apramycin sensitive colonies, representing candidate secondary recombinants, were then grown to assess rapamycin production. Non-producers were tested further by addition of exogenous trans-4-hydroxyCHCA to the production media after 24 h to confirm rapalog mutasynthetic production and verify the desired disruption of rapK. The best strain was designated BIOT-4010.

Example 2

Fermentation and Isolation of the Test Compounds 1.1 Fermentation and Isolation of 37R-Hydroxynorbornylrapamycin
Liquid Culture (Small Scale)

A single agar plug of BIOT-4010 was used to inoculate RapV7 seed media (7 mL) in a Falcon tube (50 mL) plugged with a foam bung and cultured at 28° C. and 300 rpm (2.5 cm throw) for 48 h. MD6 production media (7 mL) was inoculated with this seed culture (0.5 mL) using a wide-bore tip and fermented for 6 days at 26° C. and 300 rpm (2.5 cm throw). (1R,2R,4S)-bicyclo[2.2.1]heptane-2-carboxylic acid, (1R, 2S,4S)-bicyclo[2.2.1]heptane-2-carboxylic acid or (1R*, 2R*,4S*)-bicyclo[2.2.1]heptane-2-carboxylic acid (also known as (±)2-exo-norbornanecarboxylic acid) was added after 24 h growth in production media. Feeds were typically prepared as a 0.32 M stock solution in methanol and 50 μL was added to each tube to give a final concentration of 2 mM.

37R-hydroxynorbornylrapamycin results from feeding (1R,2R,4S)-bicyclo[2.2.1]heptane-2-carboxylic acid and has a retention time of 8.4 minutes (Method D). Feeding (1R,2S, 4S)-bicyclo[2.2.1]heptane-2-carboxylic acid results in a different hydroxynorbornylrapamycin (namely 37S-hydroxynorbornylrapamycin) with a retention time of 8.3 minutes (method D).

Fermentation (Preparative)

| Seed Conditions | |
| --- | --- |
| vessel | 2 L Erlenmeyer flask (foam bung stoppered) |
| working volume | 400 mL |
| medium | RapV7 seed medium |
| inoculum | 0.2 mL spore stock (0.05% v/v) |
| temperature | 28° C. |
| agitation | 250 rpm, 2.5 cm throw |
| aeration | aerobic |
| transfer | ~48 h |
| Fermentation Conditions | |
| vessel | 22 L Braun Biostat C Bioreactor |
| working volume | 15 L (final working volume, including seed) |
| medium | MD6/5-1 |
| inoculum | 400 mL seed (2.7% v/v) |
| temperature | 26° C. |
| agitation | ≥200 rpm (cascade DO$_2$control) |
| aeration | 7.5 L/min air (0.5 v/v/m) |
| pH | 6.40 base (NaOH) only control 0-24 h (pre-precursor) |
| | 6.90 acid (H$_2$SO$_4$) only control >24 h (post-precursor) |
| DO$_2$ | ≥30% (cascade agitation control) |
| antifoam | automatic, on demand (SAG471) |
| add d-fructose | after sterilization |
| add l-lysine | ~24 h (just before precursor) |
| add (1R*, 2R*, 4S*)-bicyclo[2.2.1]heptane-2-Carboxylic acid (also known as (±)2-exo-norbornanecarboxylic acid) | ~24 h (2 mM final conc.) |
| harvest | peak compound titre, typically 132-144 h |

Extraction and Purification

The fermentation broth was clarified by centrifugation (3000 rpm, 30 min) and the supernatant discarded if containing less than 5% total material. The cell paste was suspended in acetonitrile (2 volumes) and stirred at room temperature for 1 h. The resulting slurry was centrifuged and the supernatant decanted. This procedure was repeated, the supernatants combined, and the acetonitrile removed under reduced pressure at 40° C. The resulting aqueous slurry was extracted twice with an equal volume of ethyl acetate, the organic fractions combined and the solvent removed under reduced pressure at 40° C. The resulting crude extract was analysed for 37R-hydroxynorbornylrapamycin content and was stored at 4° C. prior to chromatographic separation.

The crude extract was dissolved in methanol:water (80:20; 200-300 mL) and extracted twice with an equal volume of hexane. The methanol:water phase was retained and solvent removed under reduced pressure at 40° C. to yield a viscous liquid residue. This material was chromatographed over flash silica gel (25×5 cm column) eluting first with chloroform (1 L) and then with volumes of 1 L each 1%, 2% and 3% methanol in chloroform. Fractions of ~250 mL were taken and analysed by HPLC. The solvent was removed from fractions containing BC319 to leave a solid residue. This was chromatographed further over flash silica gel (20×2.5 cm column) eluting with ethyl acetate:hexane (1:1). Fractions of ~200 mL were taken and analysed by HPLC. Fractions containing the peak equivalent to feeding (1R,2R,4S)-bicyclo

[2.2.1]heptane-2-carboxylic acid (see above) were pooled and the solvent was removed to leave a solid residue. This was chromatographed over reversed-phase silica gel (Waters XTerra $C_{18}$-ODS2, 10 micron particle size, 19×250 mm) eluting with a gradient of water (A) and acetonitrile (B) at a flow rate of 21 mL/min: T=0 min, 50% B; T=25 min, 100% B. Fractions containing the peak equivalent to feeding (1R,2R,4S)-bicyclo[2.2.1]heptane-2-carboxylic acid (see above) were pooled and the solvent removed in vacuo to yield 37R-hydroxynorbornylrapamycin.

Example 3

In vitro bioassays for S6 Kinase inhibition in Jurkat cell lines 37R-hydroxynorbornylrapamycin was tested for inhibition of phosphorylation of the mTOR substrate, S6K, in the Jurkat human T cell line. Jurkat T cells were treated with 37R-hydroxynorbornylrapamycin, CCI-779 (temsirolimus) or rapamycin for 4 hours at 37° C. Cells were harvested and lysed and equal amounts of cell lysate were analyzed by western blot. In this assay, 37R-hydroxynorbornylrapamycin displayed similar or more potent inhibition of S6K phosphoylation on Thr 389, as compared to other rapamycin analogues, as shown in Table 1:

TABLE 1

| Compound | Inhibition of S6 Kinase (IC50, nM) |
|---|---|
| 37R-hydroxynorbornylrapamycin | 0.19 |
| CCI-779 | 0.24 |
| Rapamycin | 0.45 |

Example 4

Pharmacokinetic Analysis

The pharmacokinetics of 37R-hydroxynorbornylrapamycin were characterized in male Sprague Dawley rats. Each group consisted of 4 fasted animals. One group was dosed with a single bolus intravenous dose of about 7.5 mg/kg of test article dissolved in DMSO/80% PEG200. The other group were dosed with a single oral dose of 32.8 mg/kg dissolved in 0.2% tween-80, 0.7% ethanol and 9.1% propylene glycol. Samples were taken at 0.25, 0.5, 1, 2, 4, 6, 8 and 24 hours and extracted as follows. Samples were extracted by aliquots (0.05 ml) of blood and verification QC samples were placed in individual wells of a 2 mL 96-well plate that was placed on ice. A 50 µL aliquot of water was added to each well containing sample. A 10 µL aliquot of spiking solution was added to the corresponding standards and 10 µL of ACN to the verification QC samples. The plate was then vortexed gently to mix. The 96-well plate was then transferred to a Tomtec Quadra 96-320 for sample extraction. A 400 µL volume of ACN containing WAY-130799 (internal standard) at 100 ng/mL was added to each well containing sample and single blank (excluding double blank samples). Double blank samples were extracted with ACN containing no IS. The plate was vortexed for 4 minutes, and then the samples were centrifuged at 3400 rpm for 5 minutes. A 400 µL volume of supernatant was transferred from each sample to a clean plate and the liquid was evaporated under N2 at 35° C. Samples were reconstituted in 150 µL of 30% ACN/water. Samples were then analysed analysed via method E and quantified against a standard curve. From the data obtained PK values could be calculated by methods known to one skilled in the art (see general methods).

Table 2 shows the pharmacokinetic parameters calculated from this study.

TABLE 2

| Compound | T½(hr) | F % (bioavailability) | Cmax (ng/mL) | Vss (L/kg) |
|---|---|---|---|---|
| 37R-hydroxynorbornylrapamycin | 7.2 | 14.1 | 215 | 17.1 |

By comparison, the half-life for rapamycin in rats is approximately 31 hours (http://www.ema.europa.eu/docs/en_GB/document library/EPAR—Scientific_Discussion/human/000273/WC500046434.pdf).

As can be seen from the data, 37R-hydroxynorbornylrapamycin exhibits a shorter half-life as compared to rapamycin in rats and may be expected similarly to do so in humans. 37R-hydroxynorbornylrapamycin is anticipated to have higher bioavailability than rapamycin.

Example 5

Evaluation in an In Vivo NZBWF1 Model of SLE

The purpose of this study was to evaluate the effects of 37R-hydroxynorbornylrapamycin, an inhibitor of the mammalian target of rapamycin (mTOR), in the NZBWF1/J mouse model of systemic lupus erythematosus. CCI-779 (temsirolimus), another mTOR inhibitor used as a positive comparator, is efficacious in ameliorating disease in this model. Briefly, 26 week old female NZBWF1/J mice were treated daily orally for 14 weeks with vehicle (Phosal), CCI-779, or 37R-hydroxynorbornylrapamycin at 1, 5, or 10 mg/kg. Half of each kidney was collected and submitted in 10% neutral buffered formalin for routine histologic processing. In addition, the other half of each kidney was frozen in OCT® medium and submitted for immunohistochemical staining for IgG, IgM, and C3. Hematoxylin and eosin (H&E)- and periodic acid-Schiff (PAS; with hematoxylin counterstain)-stained tissue sections of kidney, and tissue sections of kidney stained immunohistochemically for IgG, IgM, and C3 (with hematoxylin counterstain) were examined.

For each H&E-stained tissue section of kidney from each animal, the total numbers of inflammatory foci and intratubular proteinaceous (ie, hyaline) casts were counted in both kidneys. When inflammatory foci had coalesced, the number of individual foci were assessed by counting the number of foci of approximately 100 cells each that contributed to the coalesced foci. Morphometry was performed on PAS-stained tissue sections of kidney from each animal using a commercial image analysis software package (Image-Pro Plus v.5.1, Media Cybernetics, Silver Spring, Md.). For each PAS-stained tissue section from each animal, five (5) 40× magnification colour photomicrographs at 1388×1040 resolution were taken using a Zeiss Axiolmager. A1 microscope and a Zeiss AxioCam HRc digital microscope camera. Photomicrographs were taken of glomeruli in each renal cortex, with 1 or 2 glomeruli in each photomicrograph. A total of 10 glomeruli per animal (5 per kidney) were evaluated morphometrically by manually tracing the circumference of a glomerular tuft and determining the total area of that tuft, the total area of blue nuclear material in that tuft, and the total area of dark pink material (interpreted to be PAS-positive material) in that tuft. All areas were captured as total pixels meeting preset criteria for that parameter. Immunohistochemical staining for IgG, IgM, and C3 within glomeruli was evaluated subjectively as none (0), slight (1), mild (2), moderate (3), or severe (4). Group mean numbers of inflammatory foci and proteinaceous casts in the kidney and group mean scores for glomerular morphometry and immunohistochemical staining for IgG, IgM, and C3 within glomeruli were assessed. Summaries of group means for inflammatory foci and proteinaceous casts in the kidney; glomerularmorphometry; and immunohistochemical staining for IgG, IgM, and C3 within glomeruli; are summarized in Table 3.

This reveals that, at dose levels required for similar efficacy to CCI-779, 37R-hydroxynorbornylrapamycin leads to a reduction in hyperlipidemia, one of the major side-effects of rapamycin, CCI-779 and similar rapamycin analogues.

Example 6

Evaluation of In Vitro Inhibition of FKBP12

The purpose of this study was to evaluate the effects of 37R-hydroxynorbornylrapamycin, against FKBP12, a target for the neuroregenerative activity of rapamycins, using a PPIase assay.

| Compound | FKBP12 PPlase Ki (nM) | % CV |
|---|---|---|
| 37R-hydroxynorbornylrapamycin | 3.9 ± 0.41 | 11 |
| Rapamycin | 5.4 ± 0.35 | 6 |
| FK506 | 7.0 ± 1.0 | — |
| 37S-hydroxynorbornylrapamycin | 8.7 ± 0.7 | 8 |

TABLE 3

Summary of group means for inflammation, proteinaceous casts, glomerular morphometric parameters, and immunohistochemical staining

| Treatment | CCI-779 Phosal | CCI-779 10 mg/kg | 37R-hydroxynorbornylrapamycin 10 mg/kg | 37R-hydroxynorbornylrapamycin 5 mg/kg | 37R-hydroxynorbornylrapamycin 1 mg/kg |
|---|---|---|---|---|---|
| Total Renal inflammatory foci | 23.5 ± 3.6 | 3.4 ± 1.0 | 2.3 ± 0.6 | 4.3 ± 1.1 | 11.9 ± 2.2 |
| Total proteainaceous casts | 28.4 ± 16.4 | 2.1 ± 0.8 | 2.8 ± 0.9 | 1.0 ± 0.5 | 44.3 ± 41.3 |
| Nuclear area | 46819 ± 12832 | 32894 ± 6273 | 35605 ± 7321 | 36790 ± 6561 | 36416 ± 7421 |
| PAS positive mesangial area | 38417 ± 16053 | 18394 ± 4024 | 18641 ± 5997 | 21265 ± 5017 | 23112 ± 9058 |
| Total glomerular area | 168844 ± 44633 | 117415 ± 17281 | 122924 ± 17315 | 124261 ± 17397 | 141360 ± 42237 |
| Kidney IgG staining score | 3.4 ± 0.3 | 0.1 ± 0.1 | 1.0 ± 0.2 | 1.2 ± 0.2 | 2.3 ± 0.2 |
| Kidney IgM staining score | 3.6 ± 0.2 | 1.6 ± 0.2 | 2.2 ± 0.3 | 2.5 ± 0.3 | 3.7 ± 0.2 |
| Kidney C3 staining score | 2.9 ± 0.4 | 1.1 ± 0.1 | 2.3 ± 0.2 | 2.0 ± 0.1 | 2.8 ± 0.3 |

Figure 2:
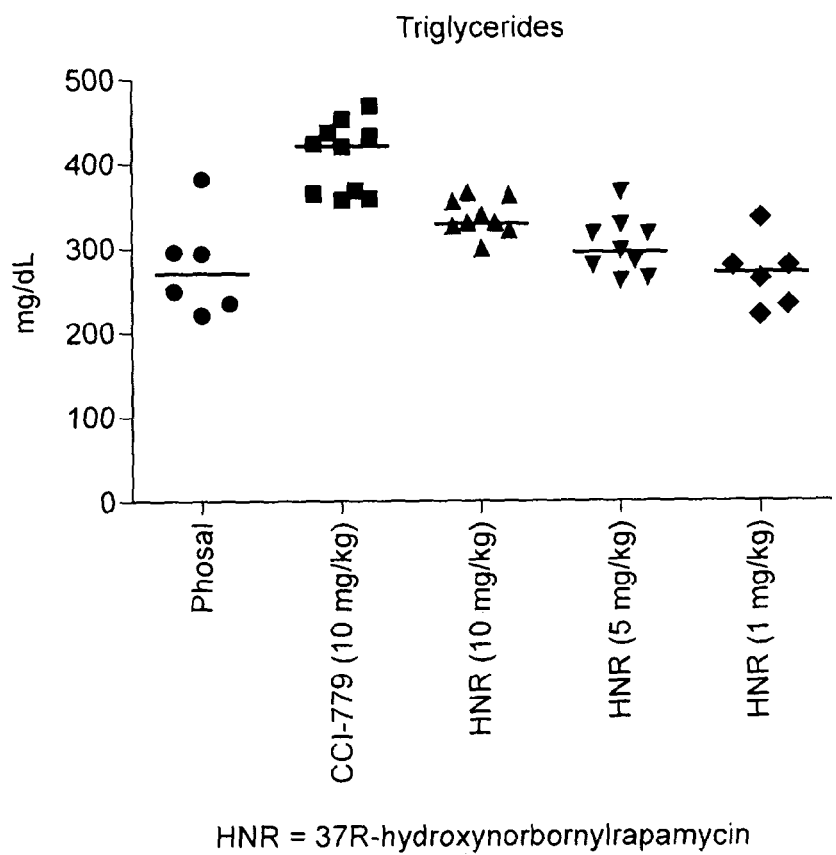
FIG. 2: Effect of 37R-hydroxynorbornylrapamycin on triglycerides in the NZBWF1 lupus model (see Example 5)
Figure 3:
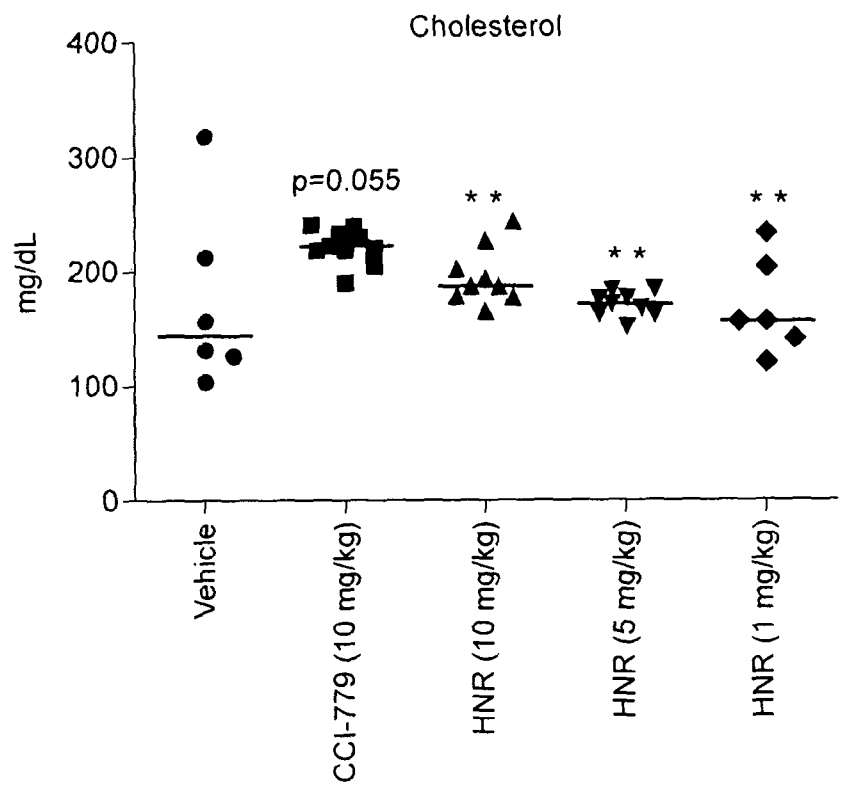
FIG. 3: Effect of 37R-hydroxynorbornylrapamycin on cholesterol in the NZBWF1 lupus model (see Example 5)
Figure 4:
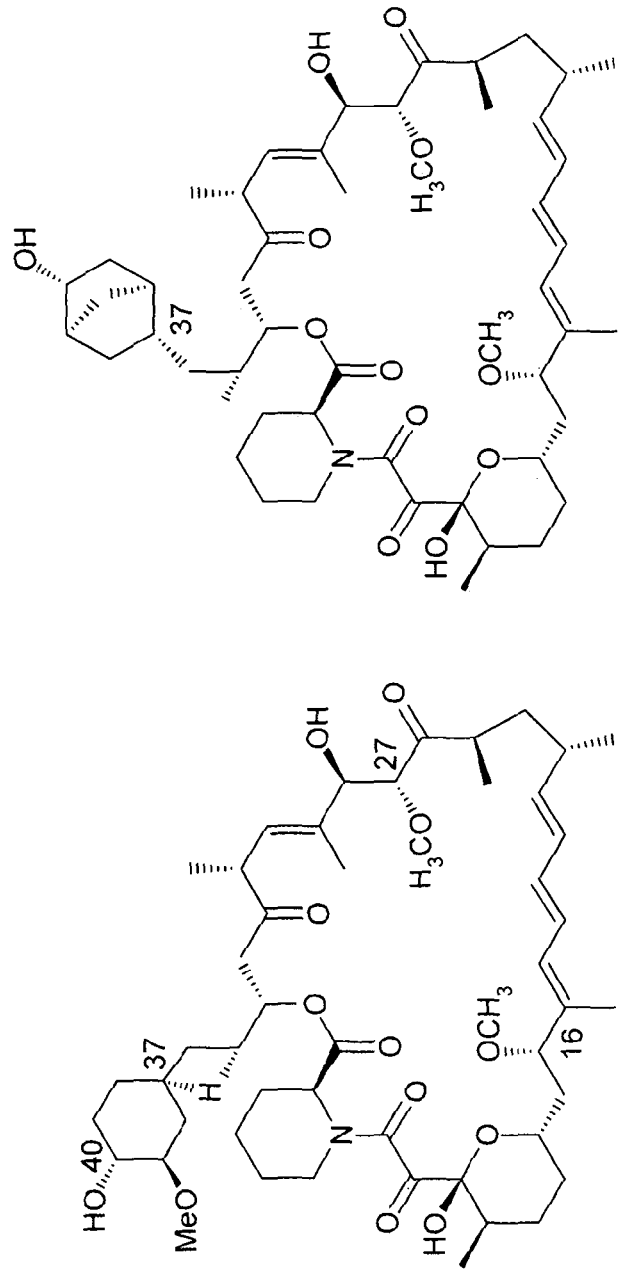
FIG. 4: Structures of rapamycin and 37R-hydroxynorbornylrapamycin

Microscopic findings in Phosal-treated mice were mononuclear inflammatory cell infiltrates in the kidneys; proteinaceous casts in renal tubules; large glomeruli with increased cellularity and increased PAS-positive mesangial matrix; and abundant immunohistochemical staining for IgG, IgM, and C3 within glomeruli. Treatment with CCI-779 at 10 mg/kg resulted in substantially lower group means for all parameters evaluated for all of these findings, Treatment with 37R-hydroxynorbornylrapamycin at similar or lower dose levels (5 and 10 mg/kg) also resulted in substantially lower group means for all parameters compared with treatment with Phosal. Beneficial effects of 37R-hydroxynorbornylrapamycin at 5 or 10 mg/kg were generally similar to those of CCI-779 (at 10 mg/kg), see FIG. 1. 37R-hydroxynorbornylrapamycin in this assay, at all dose levels, including 10 mg/kg, 37R-hydroxynorbornylrapamycin also exhibited a reduced increase in both cholesterol and triglyceride levels (FIG. 2 and FIG. 3).

Ki values are presented as ±standard error and the % CV is the coefficient of variation. As can be seen from the data, 37R-hydroxynorbornylrapamycin inhibits the PPIase activity of FKBP12 more potently than rapamycin, FK506 and the isomer 37S-hydroxynorbornylrapamycin.

Example 7

Evaluation of In Vitro Antitumour Activity in a Monolayer Assay

The purpose of this study was to evaluate the ability of 37R-hydroxynorbornylrapamycin to inhibit the glioblastoma cancer cell lines, SF268 and U87MG and the prostate cancer cell lines DU145 and PC3. Data for 37R-hydroxynorbornylrapamycin and rapamycin are the mean of two runs.

| | IC70 against cancer cell line (µM) | | | |
|---|---|---|---|---|
| | SF268 | U87MG | DU145 | PC3 |
| 37R-hydroxynorbornylrapamycin | 2.2 | 2.7 | 2.5 | 0.1 |
| Rapamycin | 2.7 | 10.0 | 4.0 | 1.3 |
| CCI-779 (Torisel) | not tested | not tested | 16.3 | 13.7 |

As can be seen, 37R-hydroxynorbornylrapamycin is more potent than rapamycin and CCI-779 at inhibiting growth of cancer cells in a monolayer assay.

REFERENCES

Alperovich, G., Rama, I., Lloberas, N., Franquesa, M., Poveda, R., Goma, M., Herrero-Fresneda, I., Cruzado, J M., Bolanos, N., Carrera, M., Grinyó, J M., and Torras, J. (2007) "New immuno suppressor strategies in the treatment of murine lupus nephritis", *Lupus*, 16:18-24.

Alvarez, M., Paull, K., Monks, A., Hose, C., Lee, J. S., Weinstein, J., Greyer, M., Bates, S., Fojo, T., (1995). "Generation of a drug resistance profile by quantitation of mdr-1/P-glycoprotein in the cell lines of the National Cancer Institute Anticancer Drug Screen", *Journal of Clinical Investigation*, 95, 2205-2214.

An, W. L., R. F. Cowburn, et al. (2003). "Up-regulation of phosphorylated/activated p70 S6 kinase and its relationship to neurofibrillary pathology in Alzheimer's disease." *Am J Pathol* 163(2): 591-607.

Andexer, J., Kengrew, S. G., et al., (2011) "Biosynthesis of the immunosuppresants FK506, FK520 and rapamycin involves a previously undescribed family of enzymes acting on chorismate", *Proc. Natl. Acad. Sci. USA*, 108:4776-4781.

Aranow, C., and Ginzler, E M. (2000) "Epidemiology of cardiovascular disease in systemic lupus erythematosus", *Lupus*, 9:166-169.

Avenoza, A., et al (1992), "Asymmetric synthesis of exo-norbornane-2-carboxylic acids", *Tetrahedron: asymmetry*, 3: 343-346.

Avramut, M. and Achim, C. L. (2002). "Immunophilins and their ligands: insights into survival and growth of human neurons." *Physiol Behav* 77(4-5): 463-8.

Baker, H., Sidorowicz, A., Sehgal, S. N., and Vézina, C. (1978) "Rapamycin (AY-22,989), a new antifungal antibiotic. III. In vitro and in vivo evaluation". Journal of Antibiotics 31, 539-545.

Bove, J., Martinez-Vicente, M., and Vila, M. (2011) "Fighting neurodegeneration with rapamycin: mechanistic insights", *Nature Reviews Neuroscience*, 12:437-452.

Boyd, M. R. and Paull, K. D., (1995). "Some Practical Considerations and Applications of the National Cancer Institute In Vitro Anticancer Drug Discovery Screen", Drug Development Research 34, 91-109, Bradl M., Hohlfeld R. (2003), "Molecular pathogenesis of neuroinflammation". J Neurol Neurosurg Psychiatry. 74:1364-70.

Brinkmann, V., Billich, A., Baumruker, T., Heining, P., Schmouder, R., Francis., G., Aradhye, S., and Burtin, P. (2010) "Fingolimod (FTY720): discovery and development of an oral drug to treat multiple sclerosis", *Nat. Rev. Drug Discovery*, 9:883-898.

Brunn, G. J., Fadden, P., Haystead, T. A., Lawrence, J. C. Jr. (1997) "The mammalian target of rapamycin phosphorylates sites having a (Ser/Thr)-Pro motif and is activated by antibodies to a region near its COOH terminus", J Biol. Chem. 272(51), 32547-32550.

Brunn, G. J., Williams, J., Sabers, C., Wiederrecht, G., Lawrence, J. C., and Abraham, R. T. (1996) "Direct inhibition of the signaling functions of the mammalian target of rapamycin by the phosphoinositide 3-kinase inhibitors, wortmannin and LY294002". EMBO Journal 15: 5256-5267.

Buttmann, M. (2010) "Treating multiple sclerosis with monoclonal antibodies: a 2010 update", *Expert Rev. Neurother.* 10:791-809.

Cao, W., and Konsoiaki, M. (2011) "FKBP immunophilins and Alzheimer's disease: A chaperoned affair", *J. Biosci.*, 36:493-498.

Chambraud, B. et al., (2010) "A role for FKBP52 in Tau protein function", *Proc. Natl. Acad. Sci.* 107:2658-2663.

Chang, S. M., P. Wen, et al. (2005). "Phase II study of CCI-779 in patients with recurrent glioblastoma multiforme." *Invest New Drugs* 23(4): 357-61.

Compston, A., & Coles, A. (2002) "Multiple sclerosis", *Lancet*, 359:1221-1231.

Crowe, A., Bruelisauer, A., Duerr, L., Guntz, P., Lemaire, M., (1999), "Absorption and intestinal metabolism of SDZ-RAD and rapamycin in rats". *Drug Metab Dispos.;* 27(5), 627-32.

Cummins, C. L., Jacobsen, W., Christians, U., Benet, L. Z., (2004) "CYP3A4-Transfected Caco-2 Cells as a Tool for Understanding Biochemical Absorption Barriers: Studies with Sirolimus and Midazolam", *The Journal of Pharmacology*, 308(1), 143-155

Dancey, J. E., (2002), "Clinical development of mammalian target of rapamycin inhibitors" Hematol Oncol Clin N Am, 16, 1101-1114.

Deleersnijder, A. et al., (2011) "Comparative analysis of different peptidyl-prolyl isomerases reveals FK506-binding protein 12 as the most potent enhancer of α-synuclein aggregation". J. Biol Chem. 286:26687-26701

Dengler W. A., Schulte J., Berger D. P., Mertelsmann R. and Fiebig H H. (1995) "Development of a propidium iodide fluorescence assay for proliferation and cytotoxicity assay". Anti-Cancer Drugs, 6, 522-532.

Donia, M., Mangano, L., Amoroso, A., Mazzarino, M C., Imbesi, R., Castrogiovanni, P., Coco, M., Meroni, P, and Nicoletti, F. (2009). "Treatment with rapamycin ameliorates clinical and histological signs of protracted relapsing experimental allergic encephalomyelitis in Dark Agouti rats and induces expansion of peripheral CD4+CD25+ Foxp3+ regulatory T cells", *J. Autoimmun.*, 33:135-140.

Dumont, F. J. and Su, Q. X. (1995). "Mechanism of action of the immunosuppressant rapamycin". Life Sciences 58(5): 373-395.

Emborg M. E., (2004) "Evaluation of animal models of Parkinson's disease for neuroprotective strategies" *J Neurosci Methods*, 139(2):121-43;

Esposito, M., Ruffini, F., Bellone, M., Battaglia, M., Martino, G., and Furlan, R. (2010). "Rapamycin inhibits relapsing experimental autoimmune encephalomyelitis by both effector and regulatory T cells modulation". *J. Neuroimmunol.*, 220:52-63

Fernandez, D., Bonilla, E., Mirza, N., Niland, B., and Peri, A. (2006) "Rapamycin reduces disease activity and normalizes T cell activation-induced calcium fluxing in patients with systemic lupus erythematosus", *Arthritis & Rheumatism*, 54:2983-2988.

Fernandez, D., and Perl, A. (2009) "Metabolic control of T-cell activation and death in SLE", *Autoimmun. Rev.*, 8:184-189.

Fernandez, D R., Telarico, T., Bonilla, E., Li, Q., Banerjee, S., Middleton, F A., Phillips, P E., Crow, M K., Oess, S., Muller-Esterl, W., and Perl, A. (2009), "Activation of mTOR controls the loss of TCRzeta in lupus T cells through HRES-1/Rab4-regulated lysosomal degradation", *J. Immunol.*, 182:2063-2073.

Fiebig H. H., Dengler W. A. and Roth T. (1999) "Human tumor xenografts: Predictivity, characterization, and discovery of new anticancer agents". In: Fiebig H H, Burger A M (eds). Relevance of Tumor Models for Anticancer Drug Development. Contrib. Oncol., 54: 29-50.

Findlay J. A, and Radics, L. (1980) *Canadian Journal of Chemistry* 58:579.

Francis, L., and Perl, A. (2009) "Pharmacotherapy of systemic lupus erythematosus", *Expert Opinon in Pharamacotherapy*, 10:1481-1494.

Gallant-Haidner H. L., Trepanier D. J., Freitag D. G., Yatscoff R. W. (2000), "Pharmacokinetics and metabolism of sirolimus". *Ther Drug Monit.* 22(1), 31-5.

Garber, K. (2008) "Infections cast cloud over Novartis' over MS therapy", *Nature Biotech.* 8:844-845.

Gerard, M. et al., (2010) "Inhibition of FK506 Binding Proteins Reduces α-Synuclein Aggregation and Parkinson's Disease-Like Pathology", J. Neurosci, 30(7):2454-2463

Gerard, M., Deleersnijder, A., Demeulemeester, J., Debyser, Z., and Baekelandt, V. (2011) "Unraveling the Role of Peptidyl-Prolyllsomerases in Neurodegeneration", *Mol. Neurobiol.*, 44:13-27.

German D. C. and Eisch A. J., (2004), "Mouse models of Alzheimer's disease: insight into treatment", *Rev Neurosci,* 15:353-69.

Goodin, D. S. et al. (2002) "Disease modifying therapies in multiple sclerosis: report of the Therapeutics and Technology Assessment Subcommittee of the American Academy of Neurology and the MS Council for Clinical Practice Guidelines", *Neurology,* 58:169-178.

Gorman, C., and Isenberg, D. (2004) "Editorial: Atherosclerosis and lupus", *Rheumatology*, 43:943-945.

Grass, G. M., Rubas, W., Jezyk, N., (1992) "Evaluation of CACO-2 monolayers as a predictor of drug permeability in colonic tissues". *FASEB Journal,* 6, A1002.

Gregory M. A., Gaisser S, Lill R. E., Hong H, Sheridan R. M., Wilkinson B, Petkovic H, Weston A. J., Carletti I, Lee H. L., Staunton J, Leadlay P F. (2004) "Isolation and characterization of pre-rapamycin, the first macrocyclic intermediate in the biosynthesis of the immunosuppressant rapamycin by *S. hygroscopicus*". *Angew Chem Int Ed Engl.* 43(19), 2551-3

Gregory M. A., Kaja A. L., Kendrew S. G., Coates N. G., Warneck N., Nur-E-Alam M., Lill R. E., Sheehan L. S., Chudley L., Moss S. J., Sheridan R. M., Quimpere M., Zhang M.-Q., Martin C. J., Wilkinson B. (2012) "Structure guided design of improved antiproliferative rapalogs through biosynthetic medicinal chemistry". *Chem. Sci.* DOI: 10.1039/C2SC21833J Gu, J. et al (2011) "Practical large-scale preparation of (±)-2-exo-norbornyl carboxylic acid and its improved isolation as the sodium salt", *Org. Process Res. Dev.,* 15: 942-945.

Hersch S. M. and Ferrante R. J., (2004), "Translating therapies for Huntington's disease from genetic animal models to clinical trials", *NeuroRx.* 1(3):298-306

Huang, S. and Houghton, P. J., 2002. "Mechanisms of resistance to rapamycins". *Drug Resist. Update,* 4(6), 378-391.

Huang, S., Bjornsti, M. A. and Houghton P. J. (2003). "Rapamycins: mechanism of action and cellular resistance." *Cancer Biol Ther* 2(3): 222-32.

Jacobs, L. D. et al. (1996) "Intramuscular interferon β-1a for disease progression in relapsing multiple sclerosis. The Multiple Sclerosis Collaborative Research Group (MSCRG)", *Ann. Neurol.,* 39:285-294.

Johnson, K. P. et al. (1995) "Copolymer 1 reduces relapse rate and improves disability in relapsing remitting multiple sclerosis: results of a phase III multicenter, double blind placebo-controlled trial. The Copolymer 1 Multiple Sclerosis Study Group", *Neurology*, 45:1268-1276.

Kahan, B. D., Chang, J. Y., and Sehgal, S. N. (1991) "Preclinical evaluation of a new potent immunosuppressive agent, rapamycin". *Transplantation* 52: 185-191.

Kang, C B., Ye, H., Dhe-Paganon, S., and Yoon, H S. (2008) "FKBP family proteins: immunophilins with versatile biological functions", *Neurosignals,* 16:318-325.

Kappos, L., Batkhof, F., Desmet, A., Trenblay, G., Brault, Y., Edan, G., Montalban, X., Polna, C., Pozzilli C., "The effect of oral temsirolimus on new magnetic resonance imaging scan lesions, brain atrophy, and the number of relapses in multiple sclerosis: results from a randomised, controlled trial". Oral abstract 0158. European Neurological Society Meeting. 18-22 Jun. 2005. Vienna, Austria.

Kingwell, E. et al. (2010) "Cardiotoxicity and other adverse events associated with mitoxantrone treatment for MS", *Neurology,* 74:1822-1826.

Kirchner, G. I., Winkler, M., Mueller L., Vidal, C., Jacobsen, W., Franzke, A., Wagner, S., Blick, S., Manns M. P., and Sewing K.-F. (2000) "Pharmacokinetics of SDZ RAD and cyclosporin including their metabolites in seven kidney graft patients after the first dose of SDZ RAD". British Journal of Clinical Pharmacology 50:449-454.

Kuhn B., Jacobsen W., Christians U., Benet L. Z., Kollman P. A. (2001), "Metabolism of sirolimus and its derivative everolimus by cytochrome P450 3A4: insights from docking, molecular dynamics, and quantum chemical calculations". *J Med Chem.* 44(12), 2027-34.

Kuo, C. J., Chung, J. K., Fiorentino, D. F., Flanagan, W. M., Blenis, J., and Crabtree, G. R. (1992) "Rapamycin selectively inhibits interleukin-2 activation of p70 S6 kinase". *Nature* 358: 70-73.

Lampen A., Zhang Y., Hackbarth I., Benet L. Z., Sewing K. F., Christians U. (1998) "Metabolism and transport of the macrolide immunosuppressant sirolimus in the small intestine". *J Pharmacol Exp Ther.* 285(3), 1104-12.

Langmann T., Mauerer R., Zahn A., Moehle C., Probst M., Stremmel W., Schmitz G. (2003) "Real-time reverse transcription-PCR expression profiling of the complete human ATP-binding cassette transporter superfamily in various tissues". *Clin Chem.* 49(2), 230-8.

Laplante A., Demeule M., Murphy G. F., Beliveau R. (2002) "Interaction of immunosuppressive agents rapamycin and its analogue SDZ-RAD with endothelial P-gp". *Transplant Proc.* 34(8), 3393-5.

Lee, J-S., Paull, K., Alvarez, M., Hose, C., Monks, A., Greyer, M., Fojo, A. T., Bates, S. E., 1994. "Rhodamine efflux patterns predict P-glycoprotein substrates in the National Cancer Institute drug screen". *Molecular Pharmacology* 46, 627-638.

Lee J. K., Bussey K. J., Gwadry F. G., Reinhold W., Riddick G., Pelletier S. L., Nishizuka S., Szakacs G., Annereau J. P., Shankavaram U., Lababidi S., Smith L. H., Gottesman M. M., Weinstein J. N. (2003) "Comparing cDNA and oligonucleotide array data: concordance of gene expression across platforms for the NCI-60 cancer cells". *Genome Biol.* 4(12), R82.

Li, A. P. (1992) "Screening for human ADME/Tox drug properties in drug discovery". *Drug Discovery Today,* 6, 357-366.

Lowden, P. A. S., (1997) Ph.D. Dissertation, University of Cambridge. "Studies on the biosynthesis of rapamycin".

Lublin, F D., Baier, M., and Cutter, G. (2003) "Effect of relapses on development of residual deficit in multiple sclerosis", *Neurology,* 61:1528-1532.

Lui, S L., Tsang, R., Chan, R W., Zhang, F., Tam, S., Yung, S., and Chan, T M. (2008) "Rapamycin attenuates the severity of established nephritis in lupus-prone NZB/W F1 mice", *Nephrol. Dial. Transplant,* 23:2768-2776.

Lui, S L., Yung, S., Tsang, R., Zhang, F., Chan, K W., Tam, S., and Chan, T M. (2008b) "Rapamycin prevents the development of nephritis in lupus-prone NZB/W F1 mice", *Lupus,* 17:305-313.

Main, E. R. G., Fulton, K. F. & Jackson, S. E. (1998). "The Context-Dependent Nature of Destabilising Mutations on the Stability of FKBP12". *Biochemistry* 37, 6145-6153.

Main, E. R. G., Fulton, K. F. & Jackson, S. E. (1999). "Folding of FKBP12: Pathway of Folding and Characterisation of the Transition State". *J. Mol. Biol.* 291, 429-444.

McAlpine, J. B., Swanson S. J., Jackson, M., Whittern, D. N. (1991). "Revised NMR assignments for rapamycin". *Journal of Antibiotics* 44: 688-690.

Meiering, E. M., Serrano, L. & Fersht, A. R. (1992). "Effect of Active Site Residues in Barnase on Activity and Stability". *J. Mol. Biol.* 225, 585-589.

Mok, C C. (2010) "Update on emerging drug therapies for systemic lupus erythematosus", *Expert Opinion in Emerging Drugs,* 15:53-70.

Moraal et al., (2010) "Long-interval T2-weighted subtraction magnetic resonance imaging: A powerful new outcome measure in multiple sclerosis trials", *Annals of Neurology,* 67: 667-675.

Morrisett, J D., Abdel-Fattah, G., Hoogeveen, R., Mitchell, E., Ballantyne, C M, Pownall, H J., Opekun, A R., Jaffe, J S., Oppermann, S., and Kahan, B D. (2002) "Effects of sirolimus on plasma lipids, lipoprotein levels, and fatty acid metabolism in renal transplant patients", *J. Lipid Research,* 43:1170-1180.

Mothe-Satney, I., Brunn, G. J., McMahon, L. P., Capaldo, C. T., Abraham, R. T., Lawrence, J. C. Jr-. (2000) "Mammalian target of rapamycin-dependent phosphorylation of PHAS-I in four (S/T)P sites detected by phospho-specific antibodies". *J Biol Chem.* 275(43), 33836-33843.

Niino, M. & Sasaki, H. (2010) "Update on the treatment options for multiple sclerosis", *Expert Rev. Clin. Immunol.,* 6:77-88.

Nishida H, Sakakibara T, Aoki F, Saito T, Ichikawa K, Inagaki T, Kojima Y, Yamauchi Y, Huang L H and Guadliana M A (1995) "Generation of novel rapamycin structures by microbial manipulations" *J Antibiot. (Tokyo)* 48(7), 657-666.

Noseworthy, J H., Lucchinetti, C., Rodriguez, M., and Weinshenker, B G. (2000) "Multiple sclerosis", *N. Engl. J. Med.* 343:938-952.

Paiva, N. L., Demain, A. L., and Roberts, M. F. (1991) "Incorporation of acetate, propionate, and methionine into rapamycin By *Streptomyces hygroscopicus*". *Journal of Natural Products* 54: 167-177.

Pardridge, (2005), "The Blood-Brain Barrier: Bottleneck in Brain Drug Development", *NeuroRx,* 2, 3-14

Patti, F. (2010) "Optimizing the benefit of multiple sclerosis therapy: the importance of treatment adherence", *Patient Prefer. Adherence,* 4:1-9.

Perin, E. C., (2005), "Choosing a Drug-Eluting Stent: A Comparison Between CYPHER and TAXUS", *Reviews in Cardiovascular Medicine,* 6 (suppl 1), ppS13-S21.

Persidis A. (1999), "Cancer multidrug resistance" Nat Biotechnol. 17: 94-5

Perl, A., Gergely, P Jr., Nagy, G., Koncz, A., and Banki, K. (2004) "Mitochondrial hyperpolarazation: a checkpoint of T cell life, death and autoimmunity", *Trends Immunol.,* 25:360-367.

Petri, M., Perez-Gutthann, S., Spence, D., and Hochberg, M C. (1992) "Risk factors for coronary artery disease in patients with systemic lupus erythematosus", *Am. J. Med.,* 93:513-519.

Poten J. et al., (1968), "Long term culture of normal and neoplastic human glia." Acta Pathol. Microbiol. Scand., 74: 465-86

PRISMS Study Group. (1998) "Randomised double-blind placebo-controlled study of interferon β-1a in relapsing/remitting multiple sclerosis", *Lancet* 352:1498-1504.

Putzki, N. et al., (2010) "Natalizumab reduces clinical and MRI activity in multiple sclerosis patients with high disease activity: results from a multicentre study in Switzerland", *Eur. Neurol.,* 63:101-106.

Raught B., Gingras, A-C. and Sonenberg, N.; (2001), "The target of rapamycin (TOR) proteins", PNAS, 98(13): 7037-7044

Ravikumar, B., R. Duden, et al. (2002). "Aggregate-prone proteins with polyglutamine and polyalanine expansions are degraded by autophagy." Hum Mol Genet 11(9): 1107-17.

Reather, J. A., (2000), Ph.D. Dissertation, University of Cambridge. "Late steps in the biosynthesis of macrocyclic lactones".

Rice, G P. et al. (2001) Interferon in relapsing-remitting multiple sclerosis. *Cochrane Database Syst. Rev.* CD002002.

Rosati, G. (2001) "The prevalence of multiple sclerosis in the world: an update", *Neurol. Sci.* 22:117-139.

Roth T., Burger A. M., Dengler W., Willmann H. and Fiebig H. H. (1999) "Human tumor cell lines demonstrating the characteristics of patient tumors as useful models for anticancer drug screening". In: Fiebig H H, Burger A M (eds). Relevance of Tumor Models for Anticancer Drug Development. Contrib. Oncol., 54: 145-156.

Ruan, B. et al., (2008) "Binding of rapamycin analogs to calcium channels and FKBP52 contributes to their neuroprotective effects", Proc. Natl. Acad. Sci. 105:33-38.

Reddy, P S., Legault, H M., Sypek, J P., Collins, M J., Goad, E., Goldman, S J., Liu, W., Murray, S., Dorner, A J., and O'Toole, T. (2008) "Mapping similarities in mTOR pathway perturbations in mouse lupus nephritis models and human lupus nephritis", *Arthritis Research & Therapy,* 10:R127.

Sathasivam, K., C. Hobbs, et al. (1999). "Transgenic models of Huntington's disease." *Philos Trans R Soc Lond B Biol Sci* 354(1386): 963-9

Sedrani, R., Cottens, S., Kallen, J., and Schuler, W. (1998) "Chemical modifications of rapamycin: the discovery of SDZ RAD". *Transplantation Proceedings* 30: 2192-2194.

Sehgal, S. N., Baker, H., and Vézina, C. (1975) "Rapamycin (AY-22,989), a new antifungal antibiotic II. Fermentation, isolation and characterization". *The Journal of Antibiotics* 28: 727-733.

Schober A. (2004), "Classic toxin-induced animal models of Parkinson's disease: 6-OHDA and MPTP" *Cell Tissue Res,* 318(1):215-24).

Shim, S. et al., (2009) "Peptidyl-prolyl isomerase FKBP52 controls chemotropic guidance of neuronal growth cones via regulation of TRPC1 channel opening", *Neuron*, 64:471-483.

Stein U., Jurchott K., Schlafke M., Hohenberger P. (2002) "Expression of multidrug resistance genes MVP, MDR1, and MRP1 determined sequentially before, during, and after hyperthermic isolated limb perfusion of soft tissue sarcoma and melanoma patients". J Clin Oncol. 20(15): 3282-92.

Steinman, L. (2005) "Blocking adhesion molecules as therapy for multiple sclerosis: natalizumab", *Nature Rev. Drug Discov.,* 4:510-518.

Stylianou, K., Petrakis, I., Vasiliki Mavroeidi, V., Stratakis, S., Vardaki, E., Perakis, K., Stratigis, S., Passam, A., Papadogiorgaki, E., Giannakakis, K., Nakopoulou, L., and Daphnis, E. (2011) "The PI3K/Akt/mTOR pathway is activated in murine lupus nephritis and downregulated by rapamycin", *Nephrol. Dial. Transplant,* 26:498-508.

Szakacs G., Annereau J. P., Lababidi S., Shankavaram U., Arciello A., Bussey K. J., Reinhold W., Guo Y., Kruh G. D., Reimers M., Weinstein J. N., Gottesman M. M. 2004, "Predicting drug sensitivity and resistance: profiling ABC transporter genes in cancer cells". Cancer Cell. 6(2):129-37.

Tanford, C. (1968). "Protein Denaturation". *Adv. Prot. Chem.* 23, 121-282.

Tanford, C. (1970). "Protein Denaturation. Part C. Theoretical models for the mechanism of denaturation". *Advances in Protein Chemistry* 24, 1-95

Tee, A. R. and Proud, C. G. (2002) "Caspase cleavage of initiation factor 4E-binding protein 1 yields a dominant inhibitor of Cap-dependent translation and reveals a novel regulatory motif". *Mol. Cell. Biol.* 22, 1674-1683

The IFNB Multiple Sclerosis Study Group. (1993) "Interferon β-1b is effective in relapsing-remitting multiple sclerosis. I. Clinical results of a multicenter, randomized, double-blind, placebo-controlled trial", *Neurology* 43:655-661.

Trepanier D. J., Gallant H., Legatt D. F., Yatscoff R. W. (1998), "Rapamycin: distribution, pharmacokinetics and therapeutic range investigations: an update". *Clin Biochem.* 31(5):345-51.

Vézina, C., Kudelski, A., and Sehgal, S. N. (1975) "Rapamycin (AY-22,989), a new antifungal antibiotic. I. Taxonomy of the producing streptomycete and isolation of the active principle". *The Journal of Antibiotics* 28: 721-726.

Vignot S, Faivre S, Aguire D, Raymond E (2005) "mTOR-targeted therapy of cancer with rapamycin derivatives", *Ann Oncol* 16: 525-537.

Volpe, D. A., Faustino, P. J., Yu, L. X., (2001) "Towards standardisation of an in vitro method of drug absorption". *Pharmacopeial Forum,* 27, 2916-2922.

Warner, L M., Adams, L M., and Sehgal, S N. (1994) "Rapamycin prolongs survival and arrests pathophysiologic changes in murine systemic lupus erythematosus", *Arthritis Rheum.,* 37:289-297.

Wu, T., Qin, X., Kurepa, Z., Kumar, K R., Liu, K., Kanta, H., Zhou, X J., Satterthwaite, A B., Davis, L S., and Mohan, C. (2007) "Shared signalling networks active in B cells isolated from genetically distinct mouse models of lupus", *Journal of Clinical Investigation,* 117:2186-2196.

Weinshenker, B. G. et al. (1989) "The natural history of multiple sclerosis: a geographically based study. I. Clinical course and disability", *Brain,* 112:133-146.

Yu, K., Toral-Barza, L., Discafani, C., Zhang, W. G., Skotnicki, J., Frost, P., Gibbons, J. J. (2001) "mTOR, a novel target in breast cancer: the effect of CCI-779, an mTOR inhibitor, in preclinical models of breast cancer". *Endocrine-Related Cancer* 8:249-258.

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:
1. A compound of formula (I)

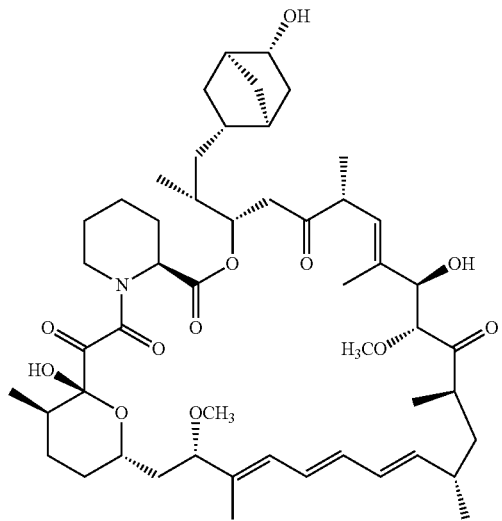

or a pharmaceutically acceptable salt thereof.

2. A compound according to claim 1 in substantially pure form.

3. A pharmaceutical composition comprising a compound of claim 1 and one or more pharmaceutically acceptable diluents or carriers.

4. The pharmaceutical composition of claim 3, wherein the compound of formula (I) is present in the composition in an amount of at least 95% w/w of the polyketide content of the composition.

5. A method of treating lupus, said method comprising administering to a subject in need thereof a compound of claim 1.

6. A method of treating multiple sclerosis, said method comprising administering to a subject in need thereof a compound of claim 1.

7. A method of preparing a compound of claim 1 said method comprising feeding a starter acid of formula (II)

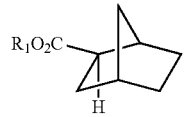

wherein $R_1$ represents H or an alkyl group,
to a rapamycin producing strain that has been genetically altered to remove or inactivate the rapK gene or homologue thereof.

8. A method of preparing a compound of formula (I) in substantially pure form according to claim 2, or a pharmaceutically acceptable salt thereof, said method comprising:
 (i) feeding a starter acid of formula (II)

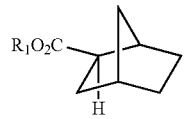

wherein $R_1$ represents H or an alkyl group,
to a rapamycin producing strain that has been genetically altered to remove or inactivate the rapK gene or homologue thereof; and
 (ii) isolating and purifying the compound of formula (I) or a pharmaceutically acceptable salt thereof.

* * * * *

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial
<220> FEATURE:
<223> OTHER INFORMATION: PCR primer

<400> SEQUENCE: 1
ccccaattgg tgtcgctcga gaacatcgcc cgggtga                             37

<210> SEQ ID NO 2
<211> LENGTH: 36
<212> TYPE: DNA
<213> ORGANISM: Artificial
<220> FEATURE:
<223> OTHER INFORMATION: PCR primer

<400> SEQUENCE: 2
cgccgcaagt agcaccgctc ggcgaagatc tcctgg                              36
```